US010856888B2

(12) United States Patent
Chenaux et al.

(10) Patent No.: US 10,856,888 B2
(45) Date of Patent: Dec. 8, 2020

(54) OFFSET REAMER DRIVER

(71) Applicant: Incipio Devices SA, St. Blaise (CH)

(72) Inventors: Fabrice Chenaux, Cortaillod (CH);
André Léchot, Orvin (CH); Thierry Gentil, Evilard (CH)

(73) Assignee: Incipio Devices SA, St. Blaise (CH)

( * ) Notice: Subject to any disclaimer, the term of this patent is extended or adjusted under 35 U.S.C. 154(b) by 391 days.

(21) Appl. No.: 15/680,518

(22) Filed: Aug. 18, 2017

(65) Prior Publication Data

US 2018/0049753 A1    Feb. 22, 2018

Related U.S. Application Data

(63) Continuation-in-part of application No. 15/355,151, filed on Nov. 18, 2016, now Pat. No. 10,660,658.

(60) Provisional application No. 62/431,908, filed on Dec. 9, 2016.

(51) Int. Cl.
| | |
|---|---|
| *A61B 17/16* | (2006.01) |
| *F16C 11/06* | (2006.01) |
| *A61B 50/30* | (2016.01) |
| *A61B 90/00* | (2016.01) |
| *A61B 17/00* | (2006.01) |

(52) U.S. Cl.
CPC ...... *A61B 17/1631* (2013.01); *A61B 17/1666* (2013.01); *A61B 50/30* (2016.02); *A61B 17/1617* (2013.01); *A61B 2017/0069* (2013.01); *A61B 2017/00473* (2013.01); *A61B 2017/00477* (2013.01); *A61B 2017/00738* (2013.01); *A61B 2050/3008* (2016.02); *A61B 2090/0813* (2016.02); *F16C 11/0609* (2013.01); *F16C 11/0614* (2013.01)

(58) Field of Classification Search
CPC ............ A61B 17/1631; A61B 17/1666; F16C 11/0609; F16D 3/32; F16D 3/40
See application file for complete search history.

(56) References Cited

U.S. PATENT DOCUMENTS

| | | | | |
|---|---|---|---|---|
| 364,503 | A * | 6/1887 | Fenner | F16D 3/40 464/134 |
| 627,203 | A * | 6/1899 | Priest | F16D 3/32 464/117 |
| 719,411 | A * | 1/1903 | Bocorselski | F16D 3/40 464/134 |
| 927,087 | A * | 7/1909 | Vanderbeek | F16D 3/40 464/134 |
| 1,034,509 | A * | 8/1912 | Ranger | F16D 3/32 464/117 |
| 2,988,904 | A * | 6/1961 | Mazziotti | F16C 23/084 464/118 |
| 3,159,013 | A * | 12/1964 | Mazziotti | F16D 3/32 464/118 |

(Continued)

OTHER PUBLICATIONS

International Search Report, International patent application No. PCT/IB2016/001143; dated Feb. 23, 2017.

*Primary Examiner* — Nicholas W Woodall
(74) *Attorney, Agent, or Firm* — Da Vinci Partners LLC; John Moetteli

(57) ABSTRACT

A system, method and/or reamer driver device provides a fully closed tube which prevents the invasion of debris and minimizes abrasion of soft tissue during use. The reamer device includes a minimum number of component assemblies, so as to permit easy replacement and minimize wear.

28 Claims, 20 Drawing Sheets

(56) References Cited

U.S. PATENT DOCUMENTS

| | | | |
|---|---|---|---|
| 3,740,969 A * | 6/1973 | Shotter | F16D 3/41 464/11 |
| 3,871,192 A * | 3/1975 | Muhr | F16D 3/32 464/134 |
| 4,037,278 A * | 7/1977 | Dotti | B63B 35/4406 441/21 |
| 5,658,290 A | 8/1997 | Lechot | |
| 6,250,858 B1 | 6/2001 | Salyer | |
| 6,540,739 B2 | 4/2003 | Lechot | |
| 6,854,742 B2 | 2/2005 | Salyer et al. | |
| 7,056,317 B2 | 6/2006 | Lechot | |
| 7,819,875 B2 | 10/2010 | Chana | |
| 7,955,320 B2 | 6/2011 | Desarzens et al. | |
| 7,955,323 B2 | 6/2011 | Lechot | |
| 8,282,639 B2 | 10/2012 | Chana | |
| 8,323,284 B2 | 12/2012 | Ferreira | |
| 8,398,639 B2 | 5/2013 | Myers et al. | |
| 2003/0216716 A1 * | 11/2003 | Desarzens | A61B 17/1666 606/1 |
| 2005/0038443 A1 * | 2/2005 | Hedley | A61B 17/162 606/91 |
| 2005/0043717 A1 * | 2/2005 | Snow | A61B 17/02 606/1 |
| 2005/0216022 A1 * | 9/2005 | Lechot | A61B 17/1631 606/81 |
| 2008/0058804 A1 | 3/2008 | Lechot et al. | |
| 2012/0022536 A1 | 1/2012 | Lualdi | |
| 2012/0023733 A1 | 2/2012 | Cannell et al. | |
| 2013/0213678 A1 | 8/2013 | Weekes | |
| 2013/0331841 A1 | 12/2013 | Roger et al. | |

* cited by examiner

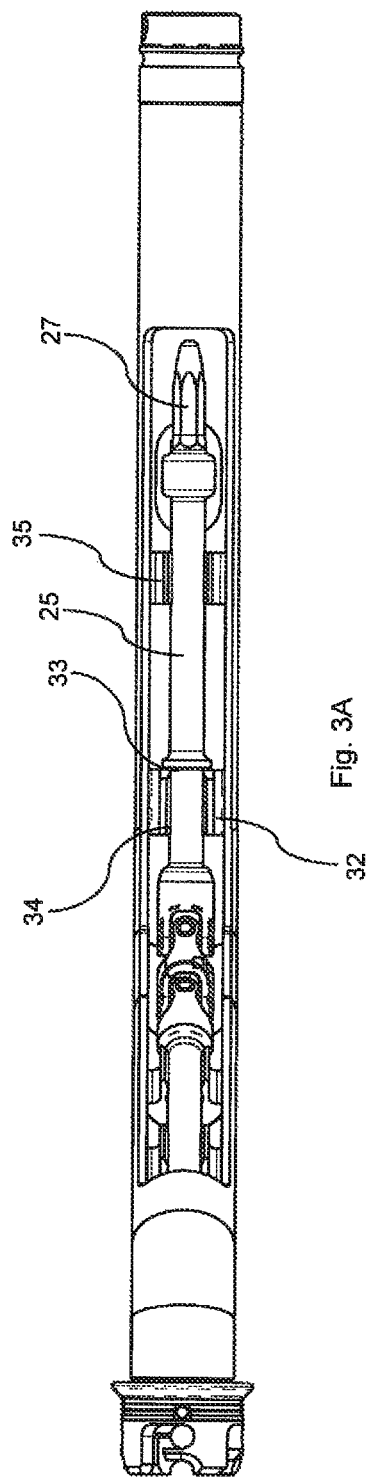
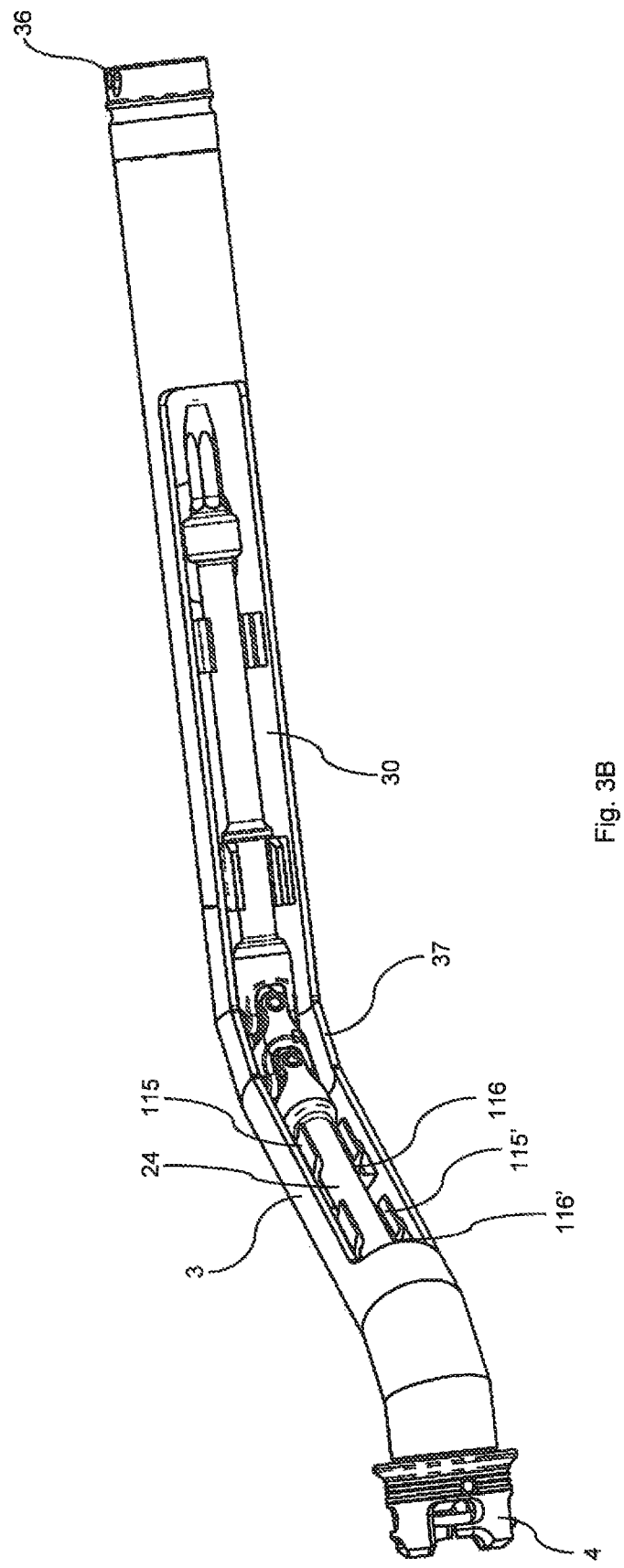

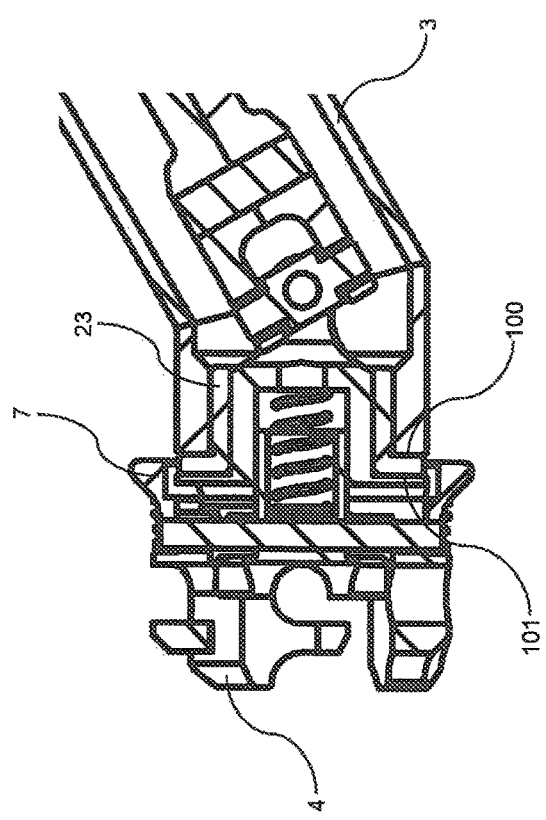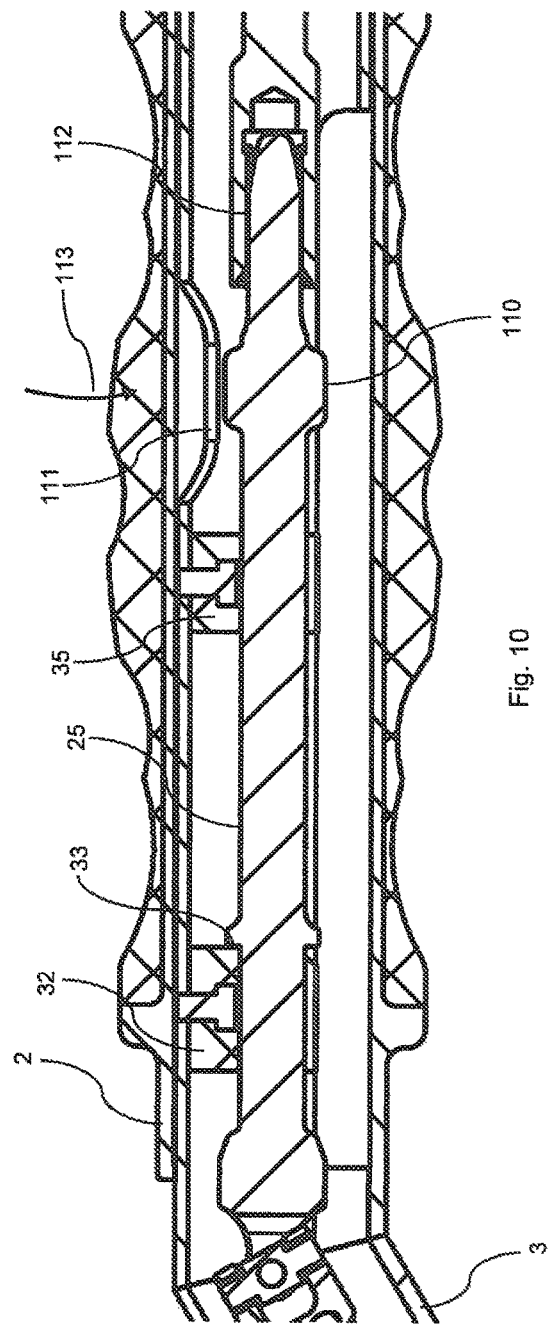

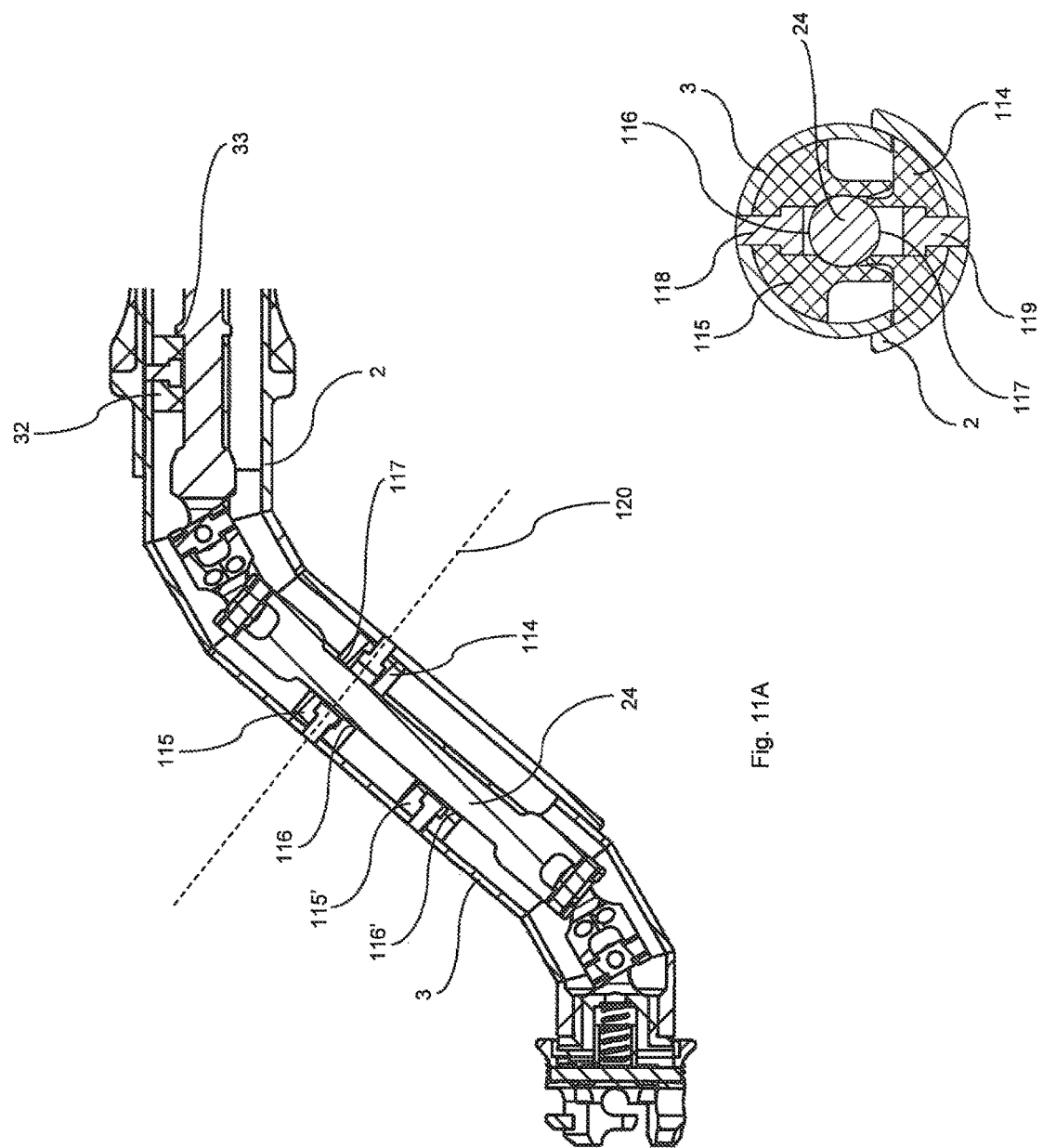

OFFSET REAMER DRIVER

CROSS REFERENCE TO RELATED APPLICATIONS

This application claims the benefit of U.S. Provisional Application No. 62/431,908, filed Dec. 9, 2016, entitled OFFSET REAMER DRIVER, U.S. Regular application Ser. No. 15/355,151, filed Nov. 18, 2016, entitled REAMER DRIVER CONNECTION as well as PCT/IB2016/001143, filed Aug. 18, 2016, entitled OFFSET REAMER DRIVER, the contents of the entirety of which are explicitly incorporated herein by reference and relied upon to define features for which protection may be sought hereby as it is believed that the entirety thereof contributes to solving the technical problem underlying the invention, some features that may be mentioned hereunder being of particular importance.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

BACKGROUND OF THE INVENTION

This invention relates to a reamer driver suitable constructed to be used to reshape the acetabulum. In particular, it relates to reamer drivers that are sealed and made up of few components.

Such reamer drivers exist. For example, U.S. patent application Ser. No. 11/536,792 to Lechot describes a reamer driver having essentially five components, namely 1) a first housing shell, 2) a second housing shell which in a clam-shell-like fashion may be juxtaposed against the first housing shell, 3) a transmission drive to be enclosed between the two housing shells, the drive having at least one universal joint and a surgical tool connector at the distal end thereof, 4) a motor shaft coupling at the proximal end thereof and 5) a handle assembly. Further, these basic components form a driver which in a fully assembled state effectively prevents debris from access in the inner workings of the driver, but they do not guarantee a near perfect sealing due largely to the long, near flat surfaces of the housing shells which can almost never be fully sealed.

There exists a need for a reamer driver in order to avoid penetration of debris and abrasion of soft tissues into the mechanism of the said reamer driver.

SUMMARY OF THE INVENTION

An improved surgical reamer driver has four basic components and a distal and proximal end. The four components include a housing assembly, a transmission drive train, a motor shaft coupling, and a handle assembly. The transmission drive train is enclosed in the housing assembly, and has a surgical tool connector at the distal end thereof. The motor shaft coupling is disposed at the proximal end thereof. A handle assembly is disposed at the proximal end thereof.

An object of the invention is to provide a driver which, in a fully assembled state, effectively prevents debris from access in the inner workings of the device. This encapsulation of the inner workings also prevents abrasion of soft tissues during use.

Another object of the invention is to provide a driver which allows an easy replacement of components e.g. when components are worn out.

Another object of the invention is to provide a transmission drive chain having at least a double universal joint linkage (unlike a normal U-joint having only one knuckle, a double U-Joint has two separate knuckles at different spaced relationships along the shaft on which the joints are disposed) that can transmit rotational movement at an angle larger than 40°. The two forks of the outermost universal joint linkages (those which are most widely spaced apart from each other) are oriented at 90° from each other.

Another object of the invention is to provide a housing that can enclose the transmission drive chain and maintain it in place with a set of bearings disposed along the chain.

Another object of the invention is to provide a driver wherein the transmission of the load applied on the motor shaft coupling is essentially transmitted to the body of the reamer handle. The load applied on the handle is also essentially transmitted to the body of the reamer handle. There is no contact between the motor shaft coupling and the handle assembly. These two cumulated loads are directly transmitted to the reamer head without compressing the universal transmission drive chain, which transmit the torque applied essentially on the motor shaft coupling.

Another object of the invention is to provide a reamer driver having a simple reamer driver connection that allows quick connect of different type of acetabular reamers from the center of the driver with a mechanism with no nukes or crannies that might trap or attract bone chips or debris. In comparison to the existing reamer driver connections described in the prior art, the locking mechanism located in the center of the driver consists of a plate whose length in the axial direction allows for axial translation without revealing spaces in which debris or chips might enter, thereby preventing such debris and bone chips from jamming the mechanism. Chips and debris is highly undesirable as such may potentially disconnect the reamer from the reamer driver. It also reduces soft tissue irritation while rotating by limiting the sharp edges of components located around the head of the reamer driver.

Another object of the invention is to provide a locking mechanism in the head of a driver which, unlike the standard lock/release function, can be locked in its open position. This allows the surgeon to insert the cutting tool through a minimal invasive opening first. Then, once locked, the reamer handle can be inserted through the same minimal invasive opening and connected to the cutting tool without activating the locking of the mechanism.

BRIEF DESCRIPTION OF THE DRAWINGS

The attached drawings represent, by way of example, different embodiments of the subject of the invention.

FIG. 3A is a bottom view of the housing assembly of the reamer driver, showing the transmission drive chain assembled.

FIG. 3B is a perspective view of the housing assembly of the reamer driver, showing the transmission drive chain assembled.

FIG. 9 is a detail of FIG. 7 showing the reamer head portion.

FIG. 10 is a detail of FIG. 7 showing the proximal portion of the transmission drive chain positioned in the body of the reamer driver.

FIG. 11A is a detail of FIG. 7 showing the distal portion of the transmission drive chain positioned in the body of the reamer driver.

FIG. 11B is a cross-section of FIG. 11A showing the transmission drive chain maintained in position by a set of bearings.

Those skilled in the art will appreciate that elements in the Figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT(S)

The following description is not intended to limit the scope of the invention in any way as they are exemplary in nature, serving to describe the best mode of the invention known the inventors as of the filing date hereof. Consequently, changes may be made in the arrangement and/or function of any of the elements described in the exemplary embodiments disclosed herein without departing from the spirit and scope of the invention.

Figure 1:
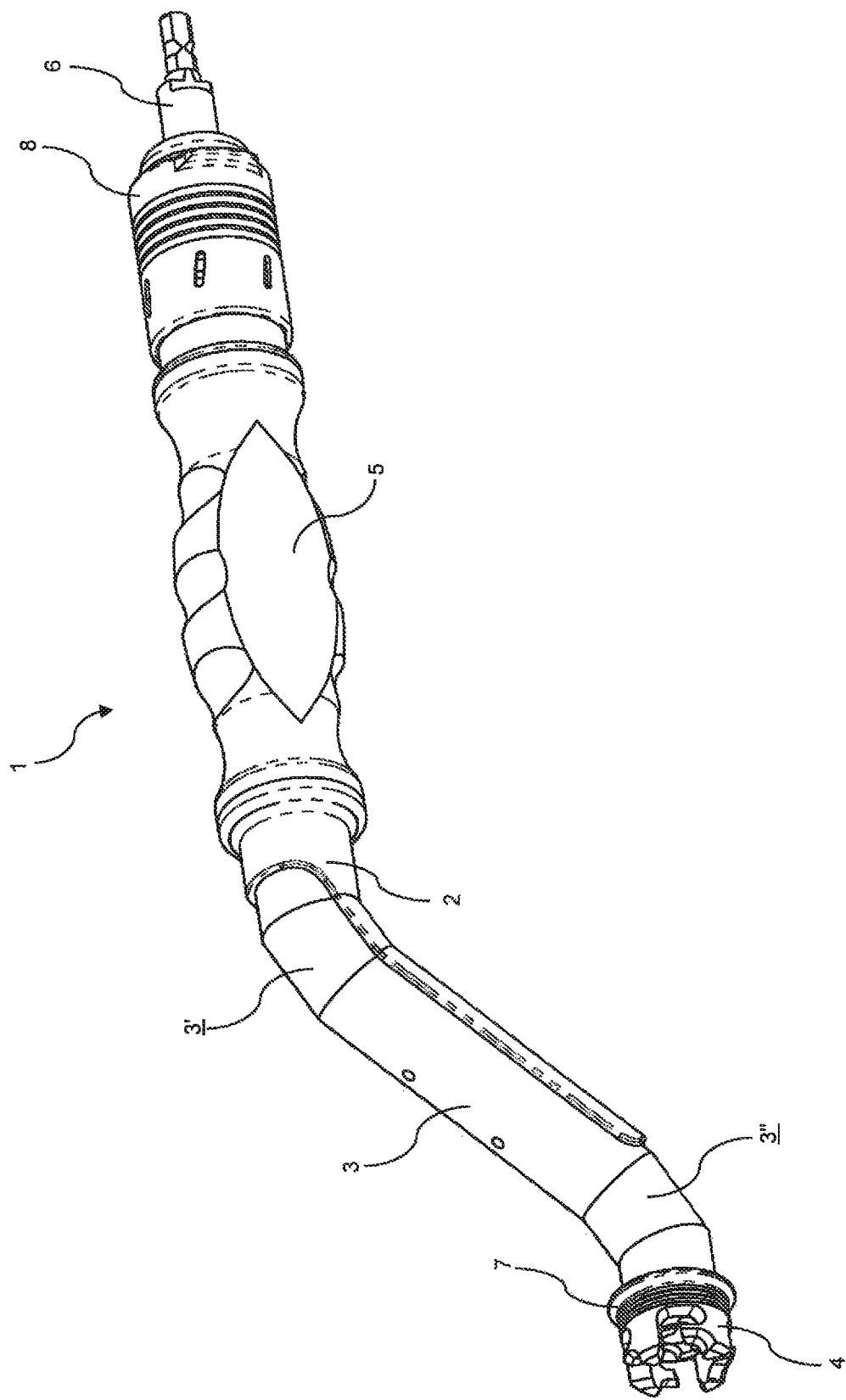
FIG. 1 is a perspective view of the fully assembled reamer driver.

Referring to FIG. 1 showing the assembled reamer driver 1. Such a reamer driver 1 is a surgical instrument used to drive bone cutting tools during minimal invasive surgeries. A distal tube 2 of the handle assembly 9 fully closing the bottom opening 30 of the body 10. This partially open tube 2 (similar to tube 3 and 10 of PCT/IB2016/001143) is part of the handle assembly 9 (as with that shown in the above-mentioned PCT, FIG. 2 and the text of the detailed description associated therewith). Housing assembly or handle assembly 10 preferably has a Z shape at position 3, a first bend at position 3', and a second base at position 3", where the central axis of the proximal transmission shaft 25 (power input) and the central axis of the distal transmission shaft 24 (power output) are not coincident. A quick tool connector 4 (such as that described in U.S. patent application Ser. No. 15/355,151), is affixed to the distal transmission shaft 24. Bone cutting tools (not shown) are connected to the said reamer head 4. Handle 5 is part of handle assembly 9. The handle 5 may be for example out of metal, plastic or silicone, and possess an anti-slippery coating, and may be shaped ergonomically, with or without anti-slippery profile. A motor shaft quick connection 6 allows the application of torque. The ring 7 allows the release of a bone cutting tool (not shown). The sleeve 8 (as with the same numbered assembly in the above-mentioned PCT) allows the release of the handle assembly 9. One of the differences to the known prior art is that the device is the fully encapsulated, avoiding penetration of debris and abrasion of soft tissues during use.

The variant shown in the figures is made out of four main components, the transmission drive chain 21 in a stand-alone, assembled unit (it is held together, mechanically locked, by the interconnection of the components), the body 10 in a stand-alone, assembled unit, the motor shaft coupling 11 in a stand-alone, assembled unit and the handle assembly 9 in a stand-alone, assembled unit.

Figure 2:
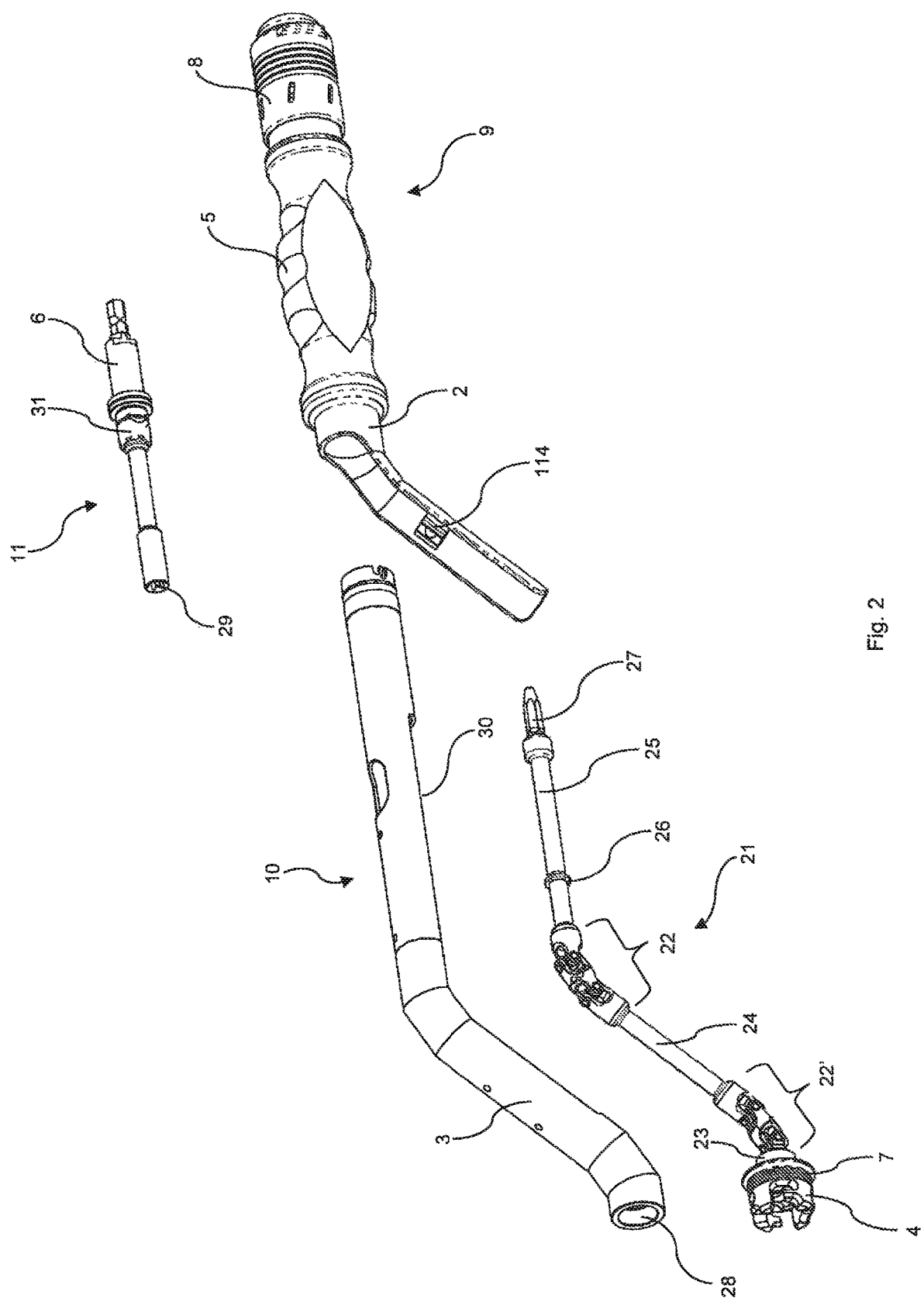
FIG. 2 is an exploded view of main components of the reamer driver.

Now referring to FIG. 2, the main components, the transmission drive chain 21, the body 10, the motor shaft coupling 11 and the handle assembly 9, separated from each other are shown, as with FIG. 2 of the above-mentioned PCT. Mechanical load applied on the handle 5 is transmitted through to the head bearing 23 and finally to the driver head 4. There is no transmission of load into the motor shaft coupling 11. The head bearing 23 may be made for example out of PEEK, carbon fiber PEEK, Teflon, PPSU, metal. The transmission drive chain typically includes universal joints 22, 22', a central transmission shaft 24, a proximal transmission shaft 25, a stop ring 26 allowing the axially positioning of the transmission drive chain when inserted into the bearing(s) 32, 35, 115 and 115', a rotational transmission feature 27 (Hex, square, triangle, . . . ) allowing transmission of the rotational torque from the motor shaft coupling 11 to the transmission drive chain 21. This feature transmits only rotational torque but not the eventual axial force applied on the motor shaft coupling 11. A front opening 28 of the housing assembly 10 where the transmission drive chain 21 can be inserted. A rotational transmission feature 29 (Hexagon, square, triangular, or any polygonal shape) to be connected with rotational transmission feature 27. A bottom opening 30 of the housing assembly 10 where the transmission drive chain 21 exits during while inserting into the housing assembly 10 and before it reaches its assembled position. Motor shaft bearing 31 may be made for example out of PEEK, carbon fiber PEEK, Teflon, PPSU or metal. One or more distal transmission drive chain bearing(s) 32, 35, 115, 115', may be made for example out of PEEK, carbon fiber PEEK, Teflon, PPSU or metal, having a snapping feature to capture the transmission shafts 24, 25 and maintain them in place. This distal transmission drive chain bearing(s) 32, 35, 115, 115' are also insuring the axial positioning of the transmission drive chain with the stop ring 26. Another distal transmission drive chain bearing 114 is assembled in the distal portion of the partially open tube 2 of the handle assembly 9 and secures the transmission drive chain in place when the handle assembly 9 is locked onto the housing assembly 10. This is particularly important with this configuration of transmission drive chain having two double u-joints linkage (unlike a normal U-joint having only one knuckle, a double U-Joint has two separate knuckles at different spaced relationships along the shaft on which the joints are disposed) because a torque applied on the rotational transmission feature 27 tends to unsnap the transmission drive chain from the bearing 115, 115'. The transmission drive chain bearing 114 cooperates with the opposite bearings 115, 115' in the housing assembly 3 to stabilize the drive train 21. The transmission drive chain bearing 114 may be made for example out of PEEK, carbon fiber PEEK, Teflon, PPSU or metal.

Now referring to FIG. 3A and FIG. 3B, whereof FIG. 3A is showing a top view of the housing assembly 10 of the reamer driver 1, showing the transmission drive chain 21 assembled and FIG. 3B is showing a perspective view of the housing assembly 10 of the reamer driver 1, showing the transmission drive chain assembled. A point of contact 33 between the stop ring 26 and the distal transmission drive chain bearing(s) 32 is avoiding axial frontward movement of the shaft 25. A point of contact 34 between the proximal transmission shaft 25 and the distal transmission drive chain bearing(s) 32, 35 insures the concentricity of the proximal transmission shaft 25 within the housing (e.g. tubes) of the housing assembly 10 and allows its rotation. A point of contact 116 between the central transmission shaft 24 and the distal transmission drive chain bearing(s) 115, 115' insures the concentricity of the central transmission shaft 24 within the housing (e.g. tubes) of the housing assembly 10 and allows its rotation. Groove 36 allowing the angular positioning of the handle in the correct orientation.

Figure 4:
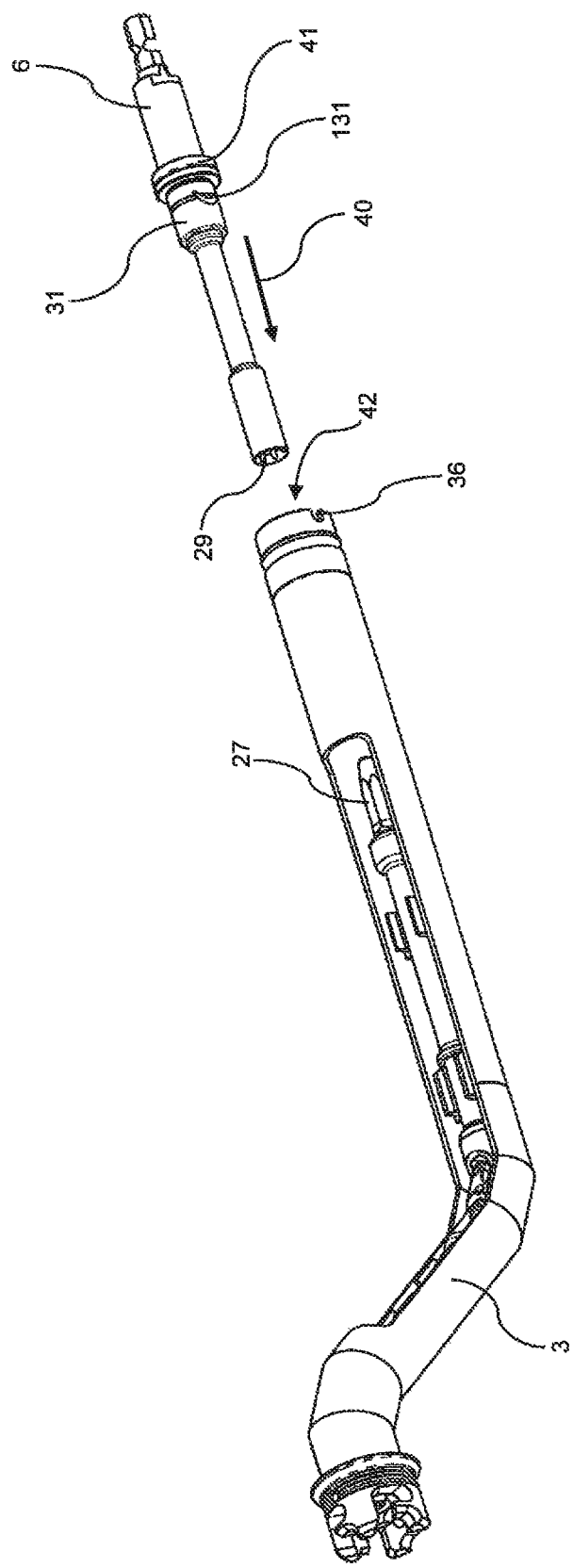
FIG. 4 is a perspective view of the housing assembly of the reamer driver, showing a part of the transmission drive chain, and showing the motor shaft coupling uncoupled from the transmission drive chain.

Now referring to FIG. 4 showing a perspective view of the housing assembly 10 of the reamer driver 1, showing a part of the transmission drive chain 21, and showing the motor shaft coupling 11 uncoupled from the transmission drive chain 21. Insertion of the motor shaft coupling 11 in direction 40 into the housing assembly 10. A retaining ring 41 allowing transmission of the axial load on the motor shaft quick connection 6 onto the motor shaft bearing 31. A back opening 42 of the housing assembly 10 where the motor shaft coupling 11 is being inserted. An elastic member 131 of the motor shaft bearing 31 retains the motor shaft coupling 11 in the housing assembly 10 while permitting rotation.

Figure 5A:
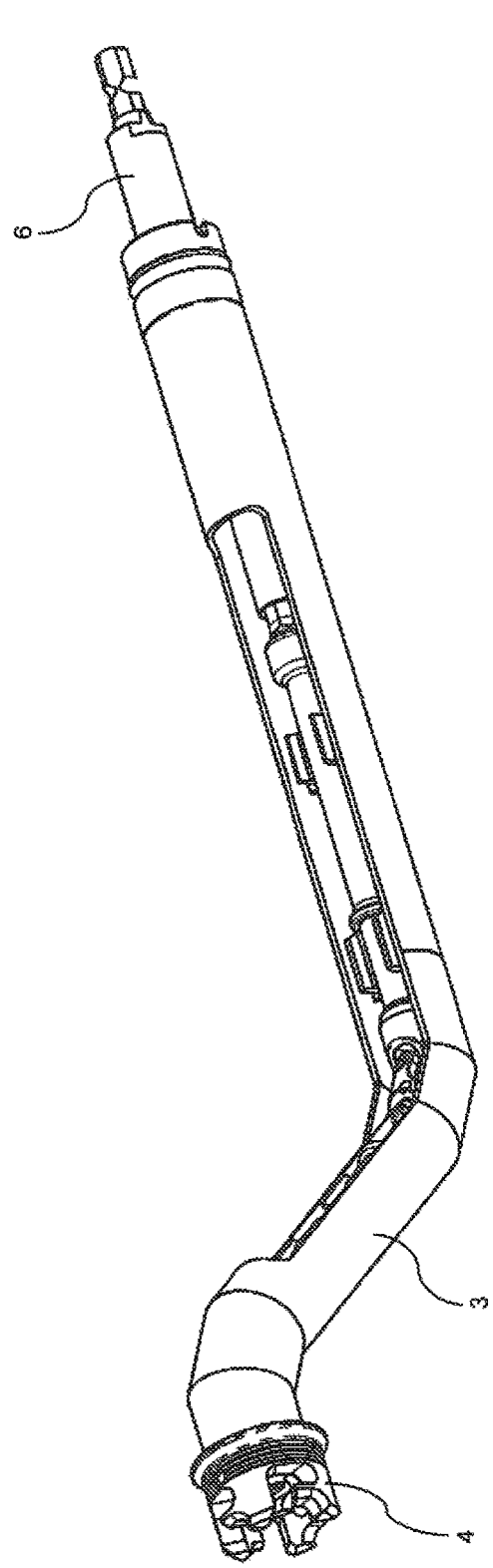
FIG. 5A is a perspective view of the housing assembly of the reamer driver, showing a part of the transmission drive chain, and showing the motor shaft coupling coupled to the transmission drive chain.

Now referring FIG. 5A showing a perspective view of the housing assembly 10 of the reamer driver 1, showing a part of the transmission drive chain 21, and showing the motor shaft coupling 11 coupled to the transmission drive chain 21.

Figure 5B:
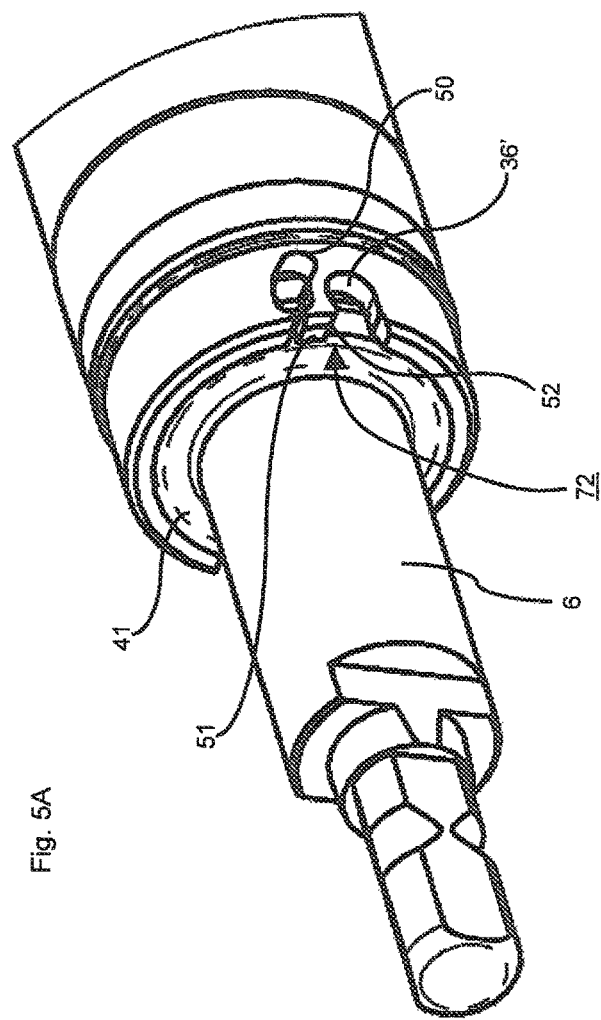
FIG. 5B is a detail of FIG. 5A showing the motor shaft coupling in the position coupled to the transmission drive chain.

Now referring FIG. 5B showing a detail of FIG. 5A showing the motor shaft coupling 11 in the position coupled to the transmission drive chain. Whereas the transmission of the load 96 applied on the motor shaft coupling 11 is made through the retaining ring 41 to the motor shaft bearing 31 and finally to the housing assembly 10. No load is transmitted into the handle assembly 9. There is no contact between the motor shaft coupling 11 and the handle assembly 9. A snap feature 72 of the invention for retaining the handle 5 against free fall or inadvertent release when disassembling the reamer handle. The snap feature 72 is enabled by creating a flexible finger retention via, for example, an adjacent relief slot 50 to pin recesses 36', which enables a raised boss 52 on a forger 51 created by this adjacent slot, to move out of the way of a pin 63 (shown in FIG. 12), and snap back thereby retaining the handle. At least a pin 63 located in the handle assembly 9 form-locks with at least one of the grooves 36 and allows the angular positioning of the handle 5.

Figure 6:
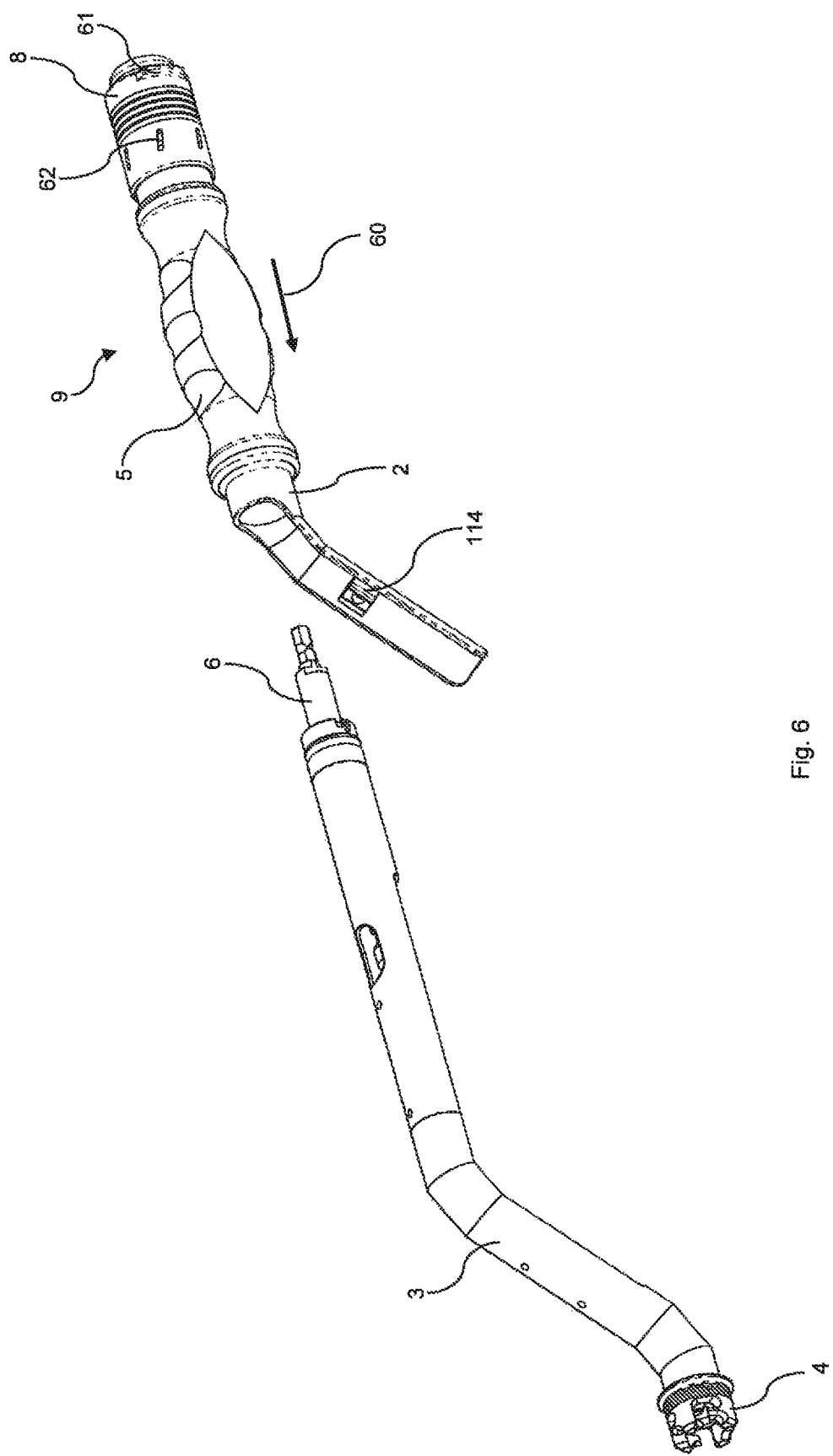
FIG. 6 is a perspective view of the housing assembly of the reamer driver, showing a part of the transmission drive chain, the motor shaft coupling coupled to the transmission drive chain, and the handle assembly uncoupled to the motor shaft coupling and uncoupled to the housing assembly of the reamer driver.

Now referring to FIG. 6 showing a perspective view of the housing assembly 10 of the reamer driver 1, showing a part of the transmission drive chain 21, the motor shaft coupling 11 coupled to the transmission drive chain 21, and the handle assembly 9 uncoupled to the motor shaft coupling 11 and uncoupled to the housing assembly 10 of the reamer driver 1. Insertion of the handle assembly 9 in direction 60 onto the assembled body 10, transmission drive chain 21 and motor shaft coupling 11. A trigger feature 61 of the sleeve 8 allowing release of the handle assembly 9. This trigger feature 61 can be made longer in order to be activated by e.g. a finger without moving the hand away from the handle 5 (similar a trigger of a pistol). One or more openings 62 into the sleeve 8 allowing circulation of water/steam during cleaning and sterilization.

Figure 7:
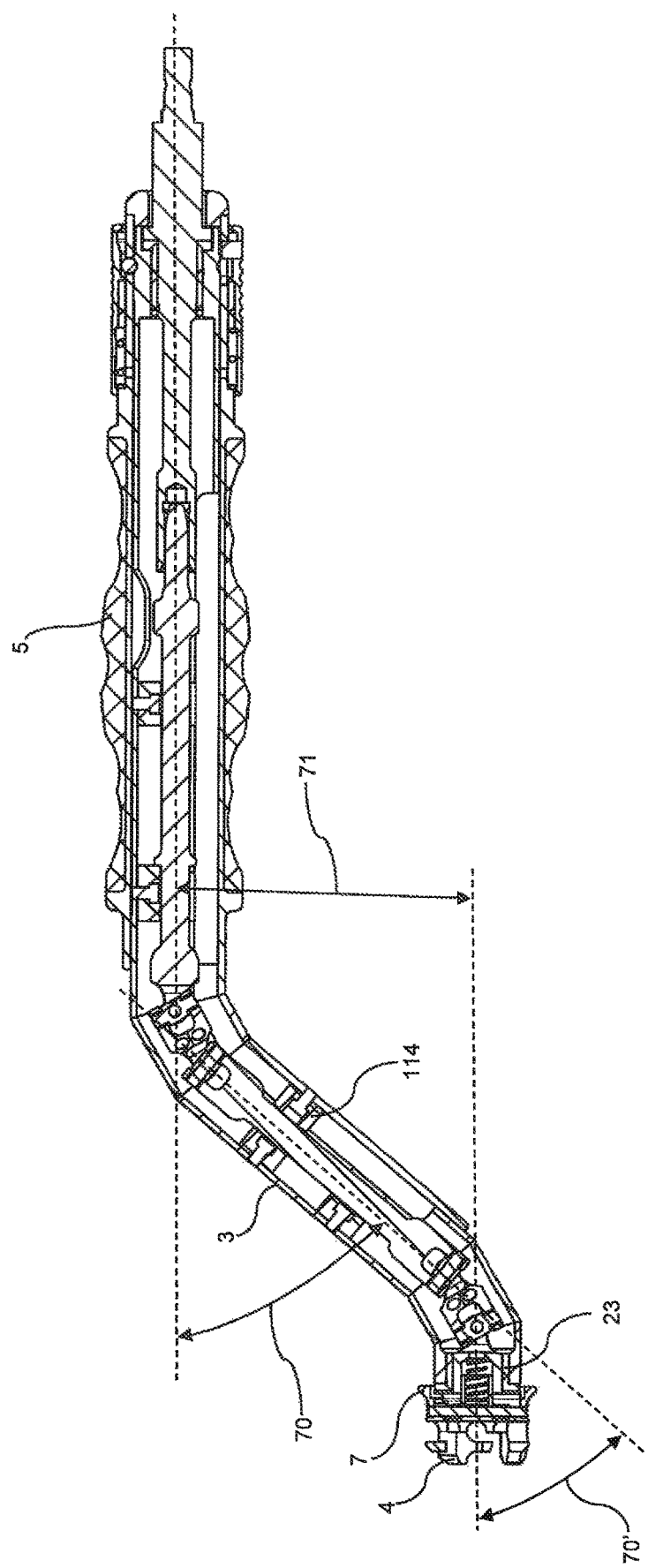
FIG. 7 is a cross-section of the fully assembled reamer driver.

Now referring to FIG. 7 showing a cross-section of the fully assembled reamer driver 1. The transmission drive chain has at least a double universal joint linkage 22 that can transmit rotational movement at an angle 70 larger than 40°. The two forks of the outermost universal joint linkages are oriented at 90° from each other to avoid a dead point while rotating. In the first embodiment of the invention, the input shaft of the transmission chain 21 is offset by a distance 71 from the output shaft. Both input and output shafts are parallel to each other (the angles 70 and 70' are identical). In a different embodiment, there might only be one double universal joint linkage 22 between the input shaft and the output shaft, wherein the input and output shafts are angled from each other.

Figure 8:
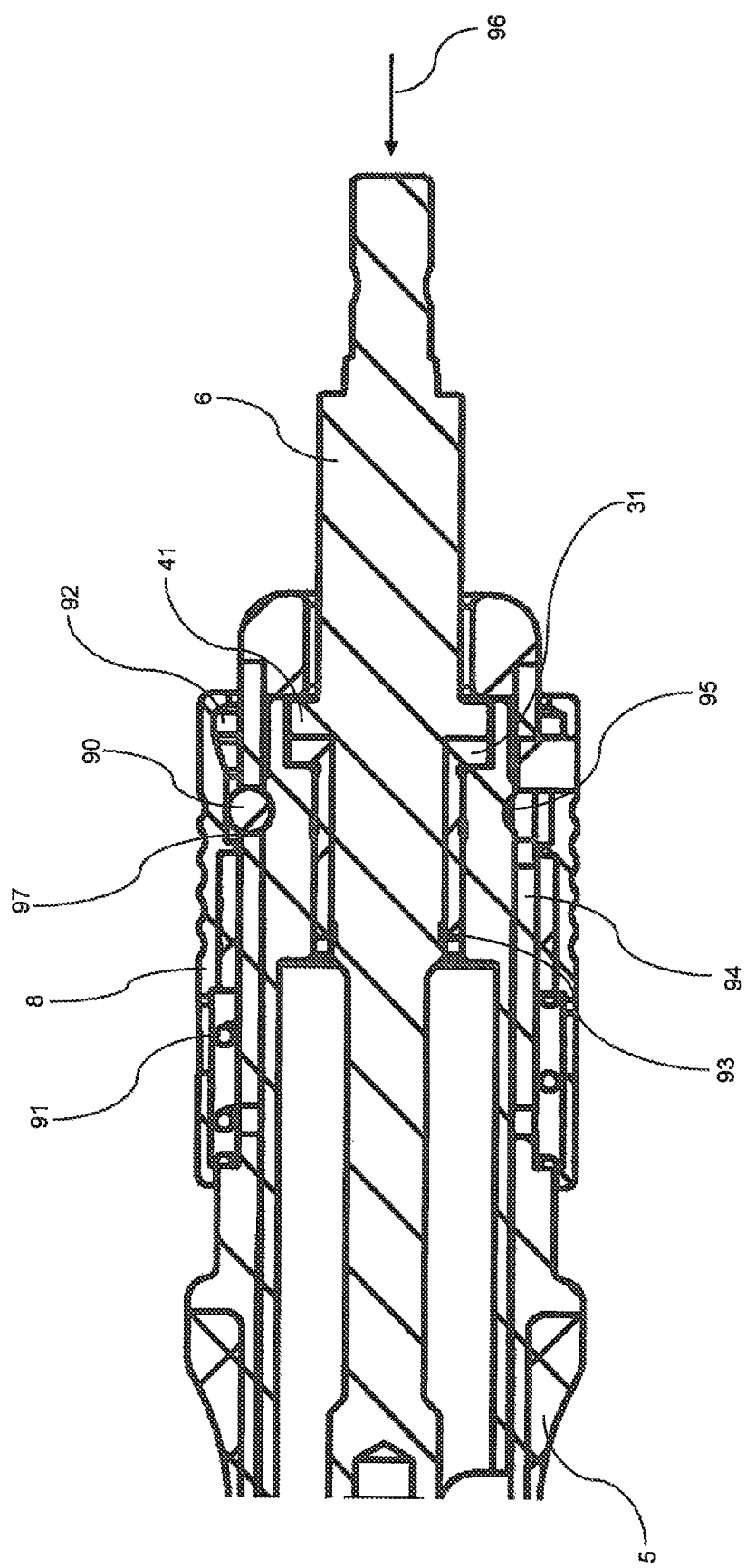
FIG. 8 is a detail of FIG. 7 showing interconnection between the handle assembly, the housing assembly, the motor shaft coupling and the transmission drive chain.

Now referring to FIG. 8 showing a detail of FIG. 7 showing interconnection between the handle assembly 9, the housing assembly 10, the motor shaft coupling 11 and the transmission drive chain 21. A ball 90 allowing connection of the handle assembly 9 with the housing assembly 10. The at least one ball 90, pushed down by profiled groove 92 of the release sleeve 8, falls into the groove 95.

A spring 91 maintaining the release sleeve 8 in its frontward position. The profiled groove 92 allowing the ball 90 to move away from the groove 95 when the release sleeve 8 is in its backward position and allowing the ball 90 to be pushed into the groove 95 when the release sleeve 8 is in its frontward position in order to lock the handle assembly 9 into the housing assembly 10. A groove 93 on the motor shaft coupling 11 where the lip of the motor shaft bearing 31, slightly smaller in diameter, falls into in order to secure the assembly of the motor shaft bearing 31 onto the motor shaft coupling 11. The groove 95 is formed into the proximal portion 94 of the housing assembly 10. One or more hole(s) 97 are formed through the distal tube 2 where they receive the locking ball(s) 90. The inside edge of the hole(s) 97 (towards the inside of the distal tube 2) has a lip slightly smaller diameter than the hole(s) 97 in order to retain the ball(s) 90 of going out.

Now referring to FIG. 9 showing a detail of FIG. 7, showing a point of contact 100 between the distal end of the body 3 (as with tube 10 of PCT/IB2016/001143, but inverted with respect to the housing 2) and the head bearing 23. An axial load applied on the housing assembly 10 (through the handle assembly 9 and through the motor connection shaft 11) is transmitted to the reamer driver head 4 through the head bearing 23. Further FIG. 9 shows a point of contact 101 between the head bearing 23 and the reamer driver head 4.

Now referring to FIG. 10 showing another detail of FIG. 7, showing an enlarged diameter portion 110 of the proximal transmission shaft 25, increasing the surface of contact when pushing the proximal transmission shaft 25 up for disassembling. A distal opening 111 in the housing assembly 3 allowing access with a finger to push the enlarged diameter portion 110 of the proximal transmission shaft 25 up. A point of contact 112 of the rotational transmission feature 27 allowing transmission of the rotational torque from the motor shaft coupling 11 to the transmission drive chain 21. This feature transmits only rotational torque but not the eventual axial force applied on the motor shaft coupling 11. An access 113 with a finger or other mean to push the proximal transmission shaft 25 up.

Now referring to FIG. 11A showing another detail of FIG. 7, showing the central portion of the transmission drive chain 21 assembled into the drive chain bearings 115, 115' of the housing assembly 3. Points of contact 116, 116' between the central transmission shaft 24 and the distal transmission drive chain bearings 115, 115' insures the concentricity of the central transmission shaft 24 within the housing (e.g. tubes) of the housing assembly 10 and allows its rotation. An optionally distal transmission drive chain bearing 114 is assembled in the distal portion of the partially open tube 2 and secures the transmission drive chain with at a point of contact 117 when the handle assembly 9 is locked onto the housing assembly 10. This distal transmission drive chain bearing 114 also insures correct snapping of the central portion of the transmission drive chain 21 into the bearings 115, 115'. In case of incorrect assembling by the user of the device, the drive chain bearing 114 will push and snap the central portion of the transmission drive chain 21 into the bearings 115, 115' when the handle assembly 9 is locked onto the housing assembly 10.

Now referring to FIG. 11B showing a cross-section view 120 of FIG. 11A, showing the transmission drive chain bearings 114, 115 insuring concentricity of the central transmission shaft 24 within the housing assembly 3. The transmission drive chain bearings 114 is assembled to the partially open tube 2 with a press-fit and/or welded pin 119. The transmission drive chain bearings 116 is assembled to the partially open tube 3 with a press-fit and/or welded pin 118.

Figure 12:
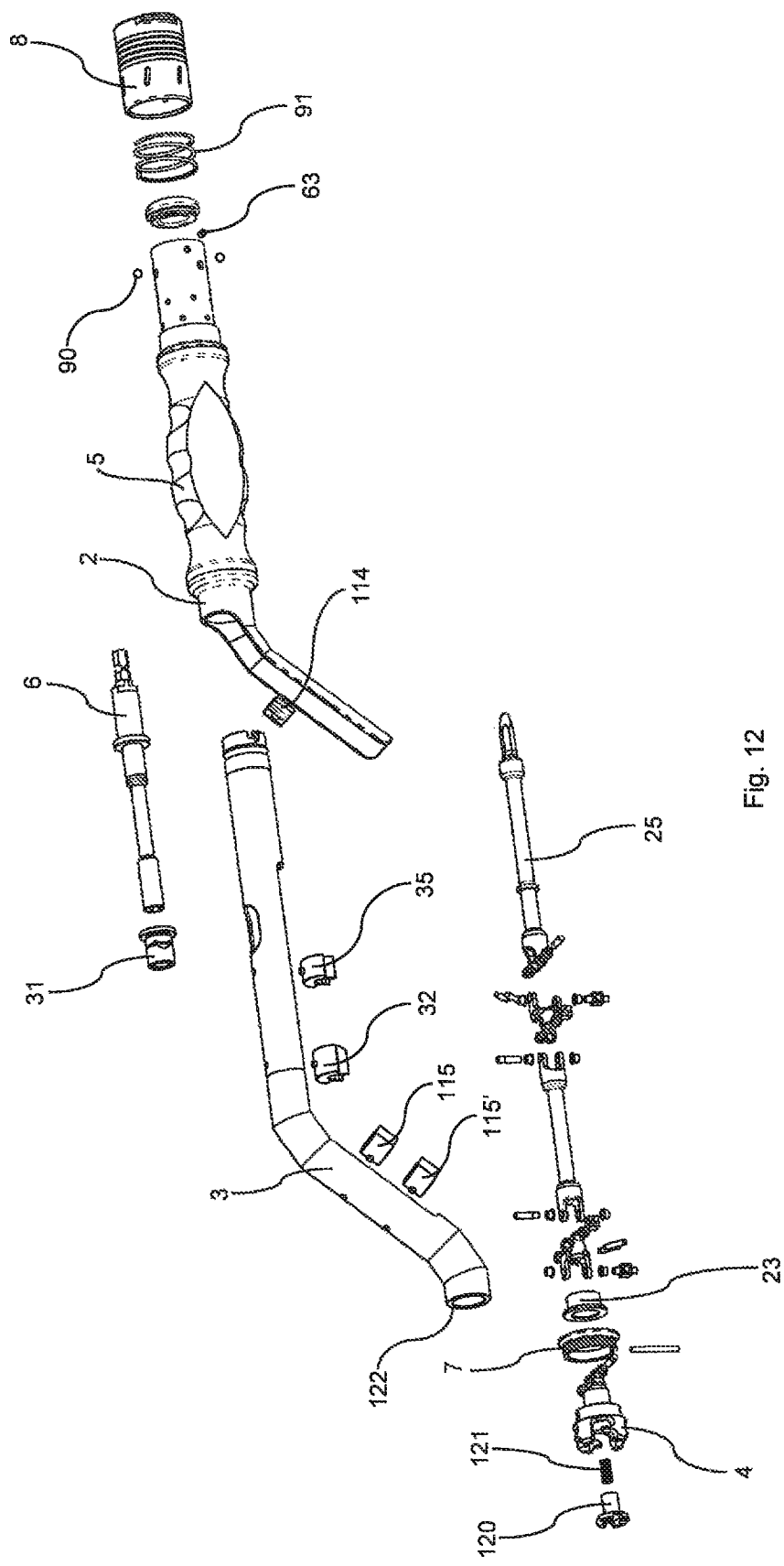
FIG. 12 is a detailed exploded view of individual components used in a variant of the invention.

Now referring to FIG. 12 showing a detailed exploded view of individual components used in a variant of the invention. A central cutting tool connection 120, a spring 121, a front face 122 of the housing assembly 10, transmitting the axial load applied on the housing assembly 10 (through the handle assembly 9 and through the motor connection shaft 11) to the reamer driver head 4 through the head bearing 23.

Figure 13:
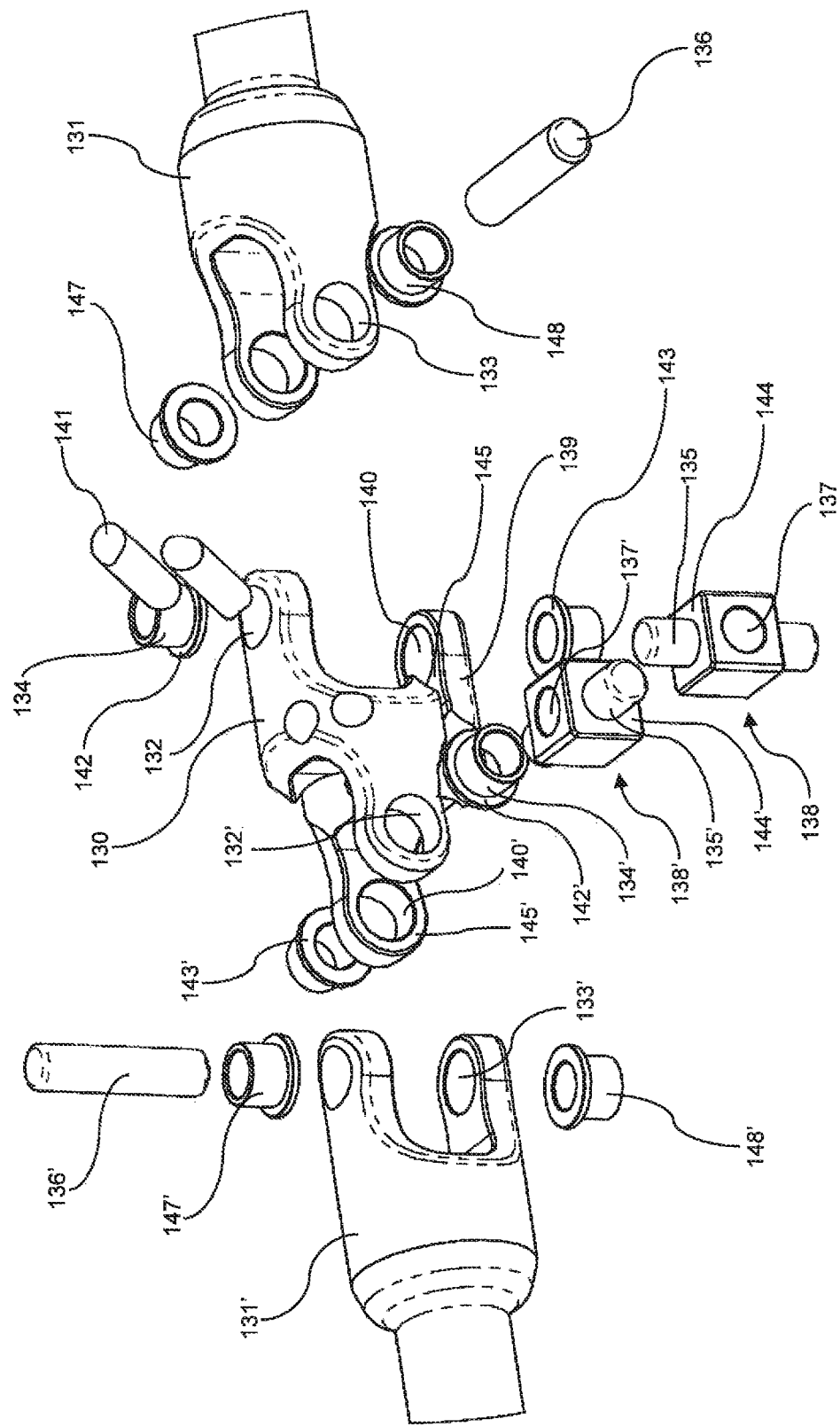
FIG. 13 is a detailed exploded view of typical components used on a universal joint as used as functional element(s) of the transmission drive chain.

Now referring to FIG. 13 showing a detailed exploded view of typical components used on a double universal joint 22 as used as functional element(s) of the transmission drive chain 21. A first half 130 and a second half 139 of the first and second forks of the double universal joint 22. The first and second forks are split in half 130, 139 to allow assembling of the central blocks 138, 138'. In a different embodiment, the first and second forks (130, 139) may be split in any number of ways, for example, in multiple pieces as long as the splits allow assembling of the central blocks 138. A third fork 131 and a fourth fork 131' of the universal joint 22. Bearing surfaces 132, 132' of the first half 130 of the first and second forks. A bearing surface 133 of the third fork 131. Bearing sleeves 134, 134', the bearing sleeves 134, 134' might be made for example out of PEEK, carbon fiber PEEK, Teflon, PPSU or metal. Cylindrical extensions 135 of the central block 138 allowing its rotation with the two halves 130, 139 of the first fork. Cylindrical extensions 135' of the central block 138' allowing its rotation with the two halves 130, 139 of the second fork. A cylindrical pin 136 allowing rotation of central block 138 with the third fork 131. The cylindrical pin 136 is press fit into the central hole 137 of the central block 138. A central hole 137 of the central block 138. A cylindrical pin 136' allowing rotation of central block 138' with the fourth fork 131'. The cylindrical pin 136' is press fit into the central hole 137' of the central block 138'. A central hole 137' of the central block 138'. Bearing surface 140 of the second half 139 of the first fork. Bearing surface 140' of the second half 139 of the second fork. Positioning pins 141, press fit into the two halves 130, 139 to maintain the two halves 130, 139 together. Inner bearing surfaces 142 of the bearing sleeves 134 insuring positioning and low friction with the inner surfaces 145 of the first fork. Outer bearing surfaces 143 of the bearing sleeves 134 insuring positioning and low friction with the side surfaces 144 of the central block 138. Side surfaces 144 of the central block 138, adjacent to the cylindrical extension 135. Inner bearing surfaces 142' of the bearing sleeves 134' insuring positioning and low friction with the inner surfaces 145' of the second fork. Outer bearing surfaces 143' of the bearing sleeves 134' insuring positioning and low friction with the side surfaces 144' of the central block 138'. Side surfaces 144' of the central block 138', adjacent to the cylindrical extension 135'.

Part of the invention is the use of double universal joints 22 having eight bearing sleeves 134 for this kind of devices. It is expected to highly increase the life of the universal joint 22 by reducing the friction and therefore the wear. More traditional universal joints have metal on metal friction.

Figure 14:
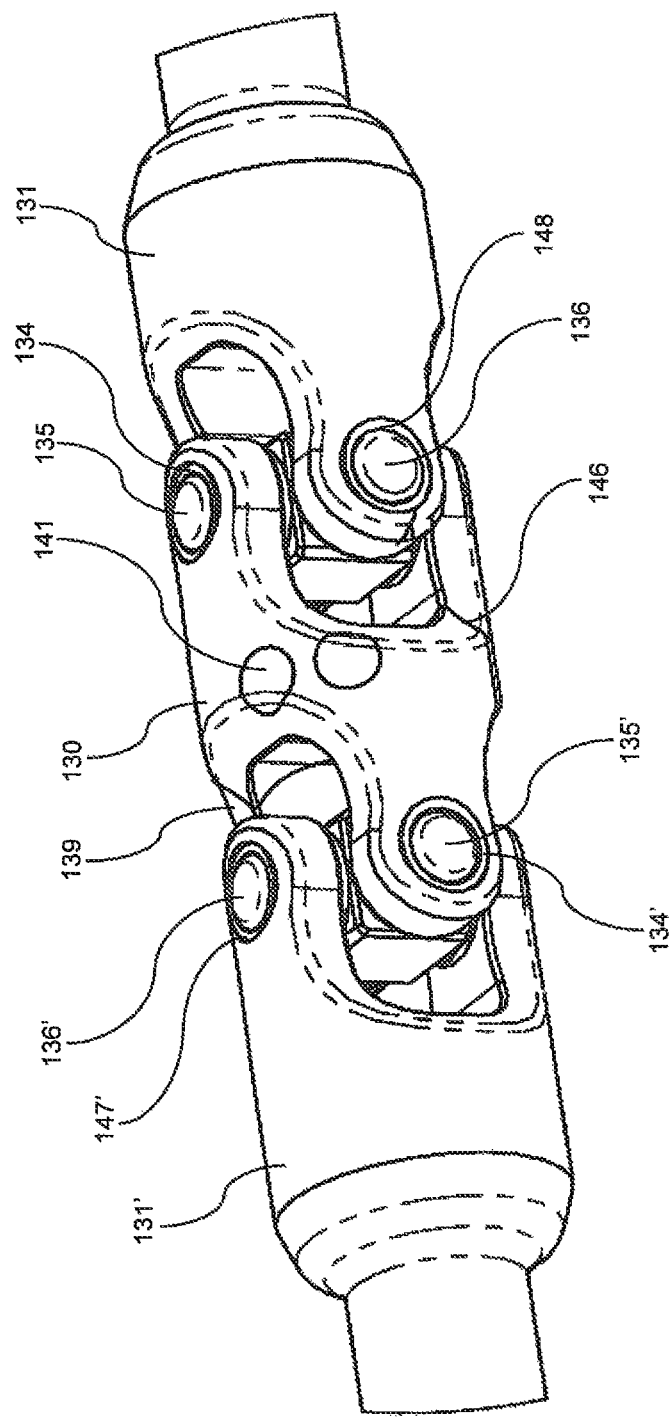
FIG. 14 is a perspective view of a universal joint as used as functional element(s) of the transmission drive chain.

Now referring to FIG. 14 showing a perspective view of a double universal joint 22 as used as functional element(s) of the transmission drive chain 21. A contact surface 146 between the two halves 130, 139 of the first and second forks. In addition to the pin 141, the two halves can be secured together by welding, gluing. Another object of this invention is the offset angulation of the first and second fork from each other. The known prior art shows the first and second forks of a double universal joint being in a mirror position from each other, forming an H-shape.

Figure 15:
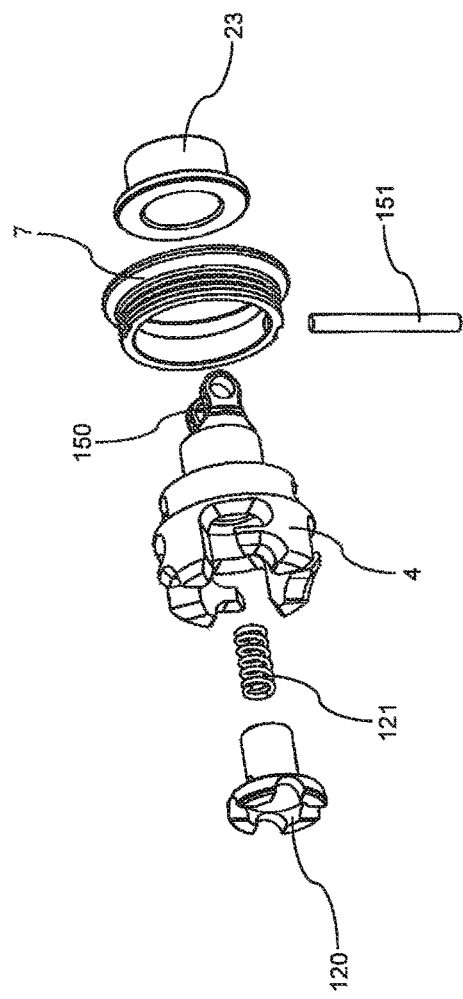
FIG. 15 is a detailed exploded view of the reamer head portion.

Now referring to FIG. 15 showing a detailed exploded view of the reamer head portion. A retaining rib 150 allowing the retention of the head bearing 23 once assembled onto the reamer head 4. This retaining rib 150 is positioned in such way to allow slight translation movement of the head bearing 23 for easier cleaning but to retain the head bearing 23 of falling off. A pin 151 connecting the ring 7 with the central cutting tool connection 120 together, as also visible in FIG. 10.

Figure 16:
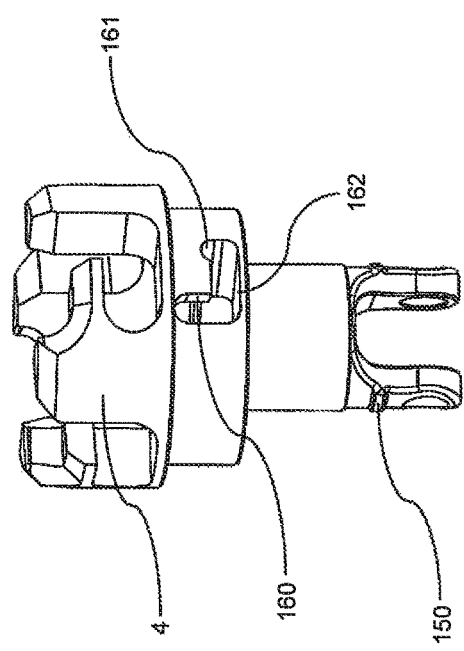
FIG. 16 is a perspective view of the reamer head portion.

Now referring to FIG. 16 showing a perspective view of the reamer head portion. An elongated groove 160 allowing the cutting tool locking mechanism (ring 7, pin 151 and central cutting tool connection 120) to slide backward/frontward in direction 181 in order to release/lock the cutting tool. The cutting tool locking mechanism is spring loaded with spring 121 in its locked position. The elongated groove 161 allowing the cutting tool locking mechanism (ring 7, pin 151 and central cutting tool connection 120) to be locked in the release (open) position. A channel 162 allowing the cutting tool locking mechanism (ring 7, pin 151 and central cutting tool connection 120) to be switched between the release/lock movement and the locked open position by rotation 180.

Figure 17:
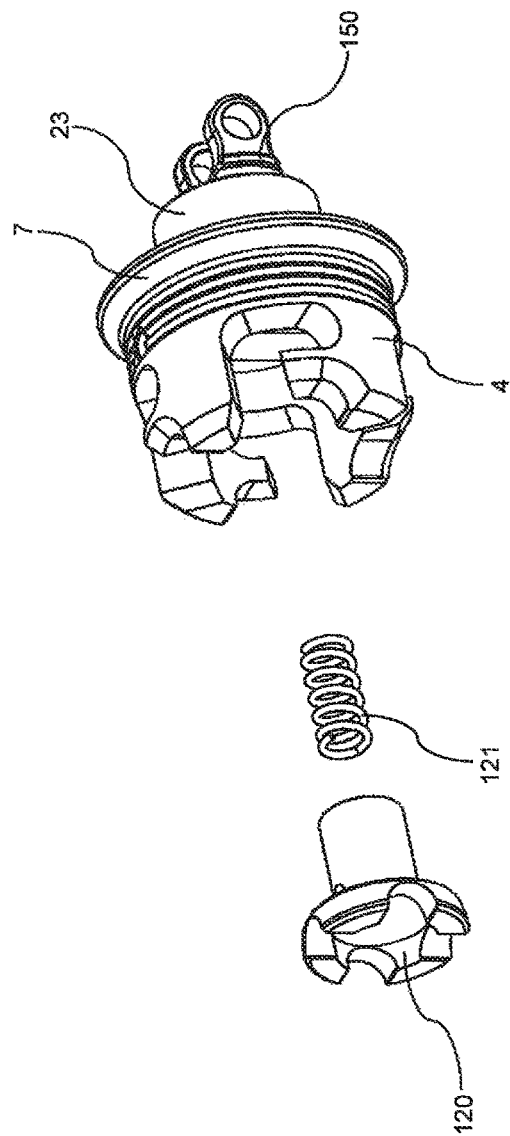
FIG. 17 is a partially exploded view of the reamer head portion.

Now referring to FIG. 17 showing a partially exploded view of the reamer head portion. A central cutting tool connection 120, a spring 121, a reamer head 4.

Figure 18:
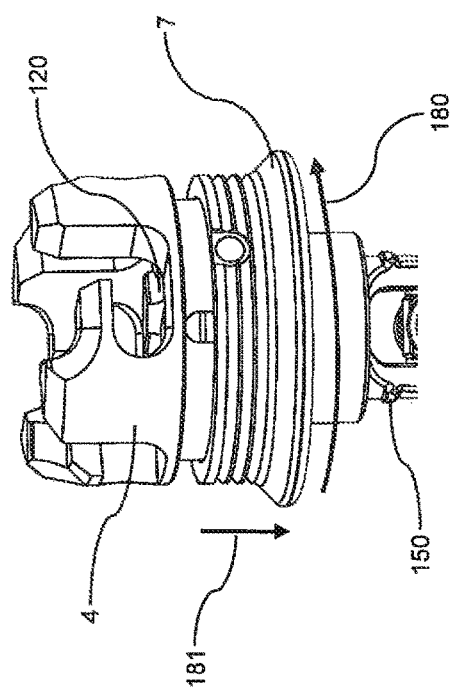
FIG. 18 is a perspective view of the reamer head connection in the lock open position.
Figure 19:
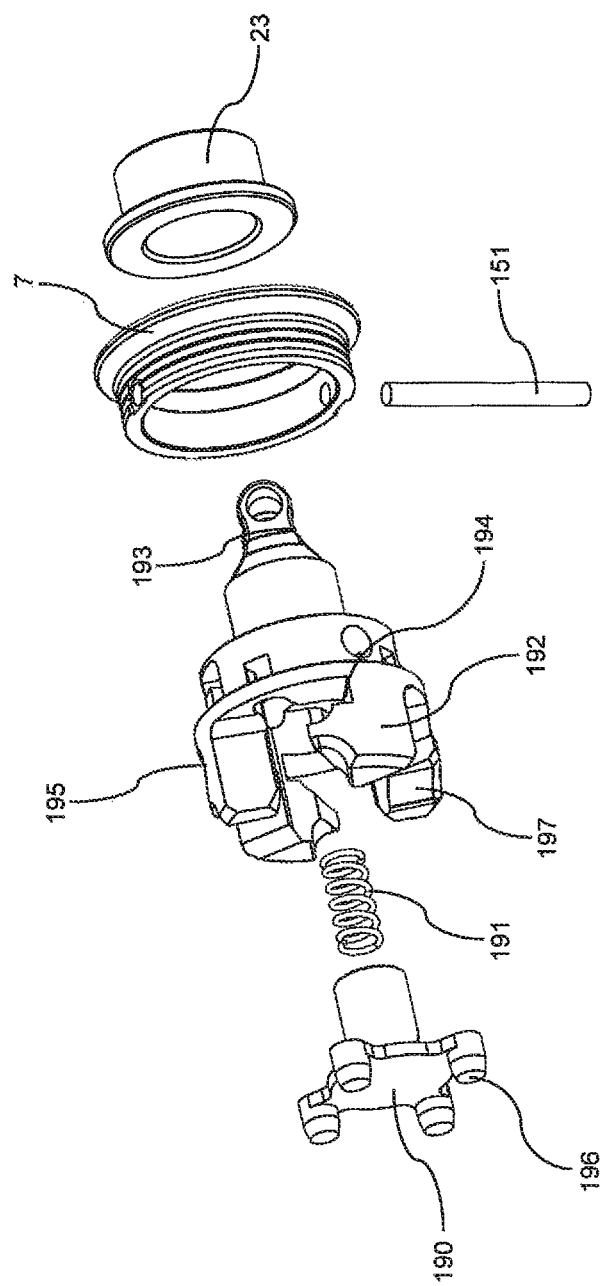
FIG. 19 is a multiple reamer coupling of the invention is shown.
Figure 20:
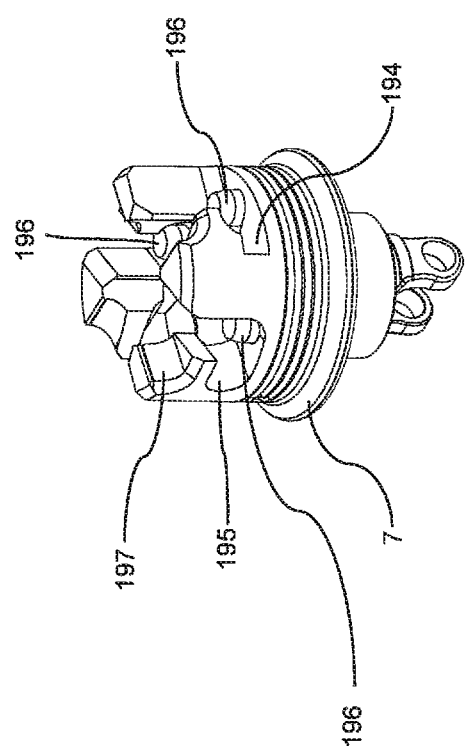
FIG. 20 is a multiple reamer coupling of the invention is shown.

Now referring to FIG. 18 showing a perspective view of the reamer head connection in the lock open position, indicating the direction 180 of the rotation of the ring 7 (and therefore the tool locking mechanism) to switch between the release/lock movement and the locked open position. Indicating the direction 181 of a pull movement of the ring 7 (and therefore the tool locking mechanism) to release the cutting tool. Referring now to FIGS. 19 and 20, an alternate multiple reamer coupling of the invention, used to connect with the reamer bar 211 shown in FIG. 30, has a locking head 190 with at least one pin 196 located in such a way as to close the L-shaped openings 195 and therefore capture the connecting bars of the acetabular reamer once engaged into it in order to maintaining the reamer firmly connected to the driver. Different L-shaped openings 194 may be used to connect non-cylindrical connecting bars of different types of acetabular reamers. As shown is these figures, both rectangular L-shaped openings 194 and cylindrical L-shaped openings 195 are used in the same reamer head in order to connect different acetabular reamers having either rectangular or cylindrical connecting bars.

A further alternate embodiment of the multiple reamer coupling of the invention has strategically located pins 196 lock the cutting tool in place.

Figure 21:
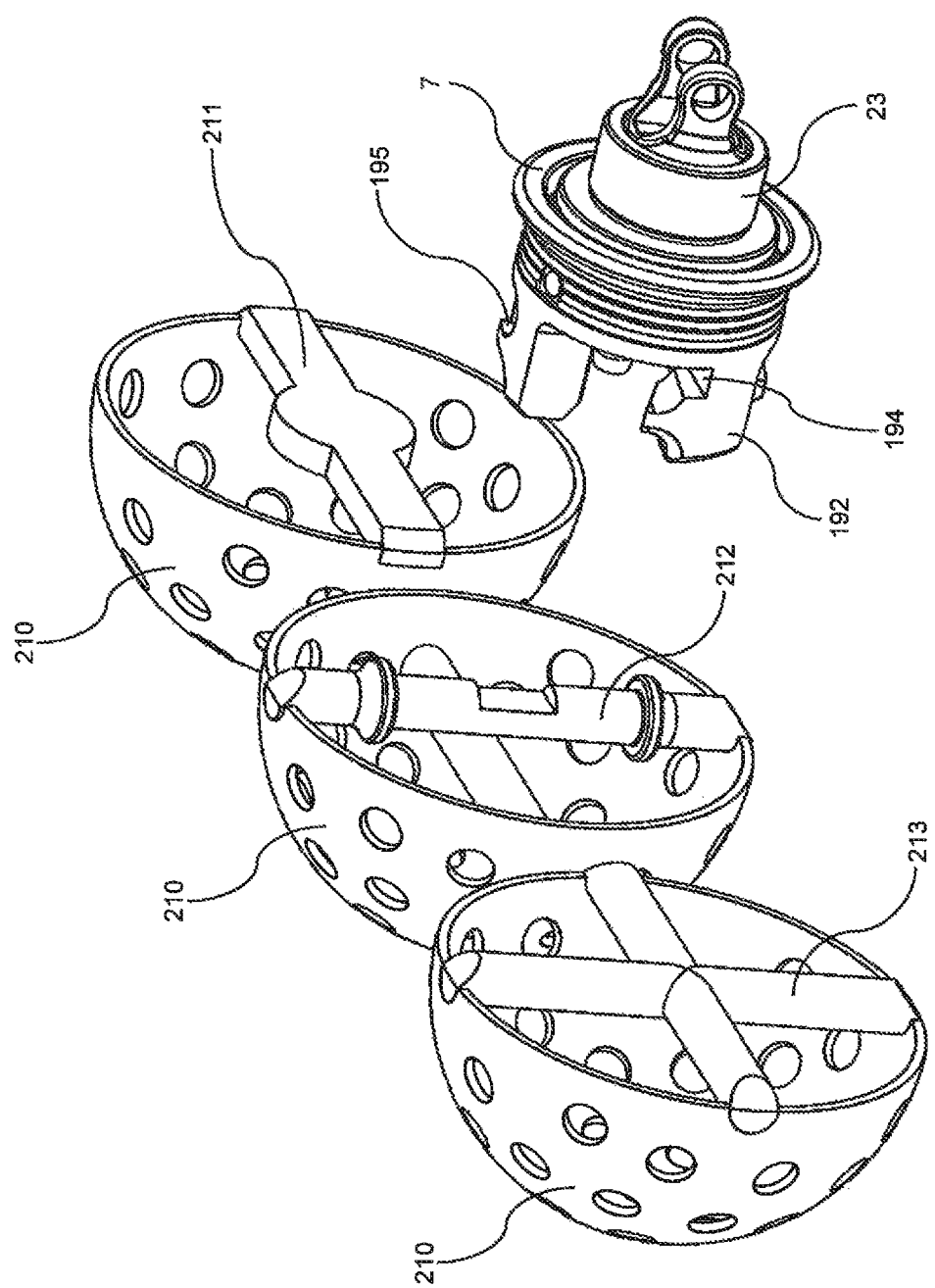
FIG. 21 is a multiple reamer coupling of the invention is shown.

Referring now to FIG. 21, the embodiment of FIG. 20 may be configured, based on the location of the locking pins, to lock three different types of tools 210, having three different types of interfaces 211, 212, and 213, respectively.

Figure 22:
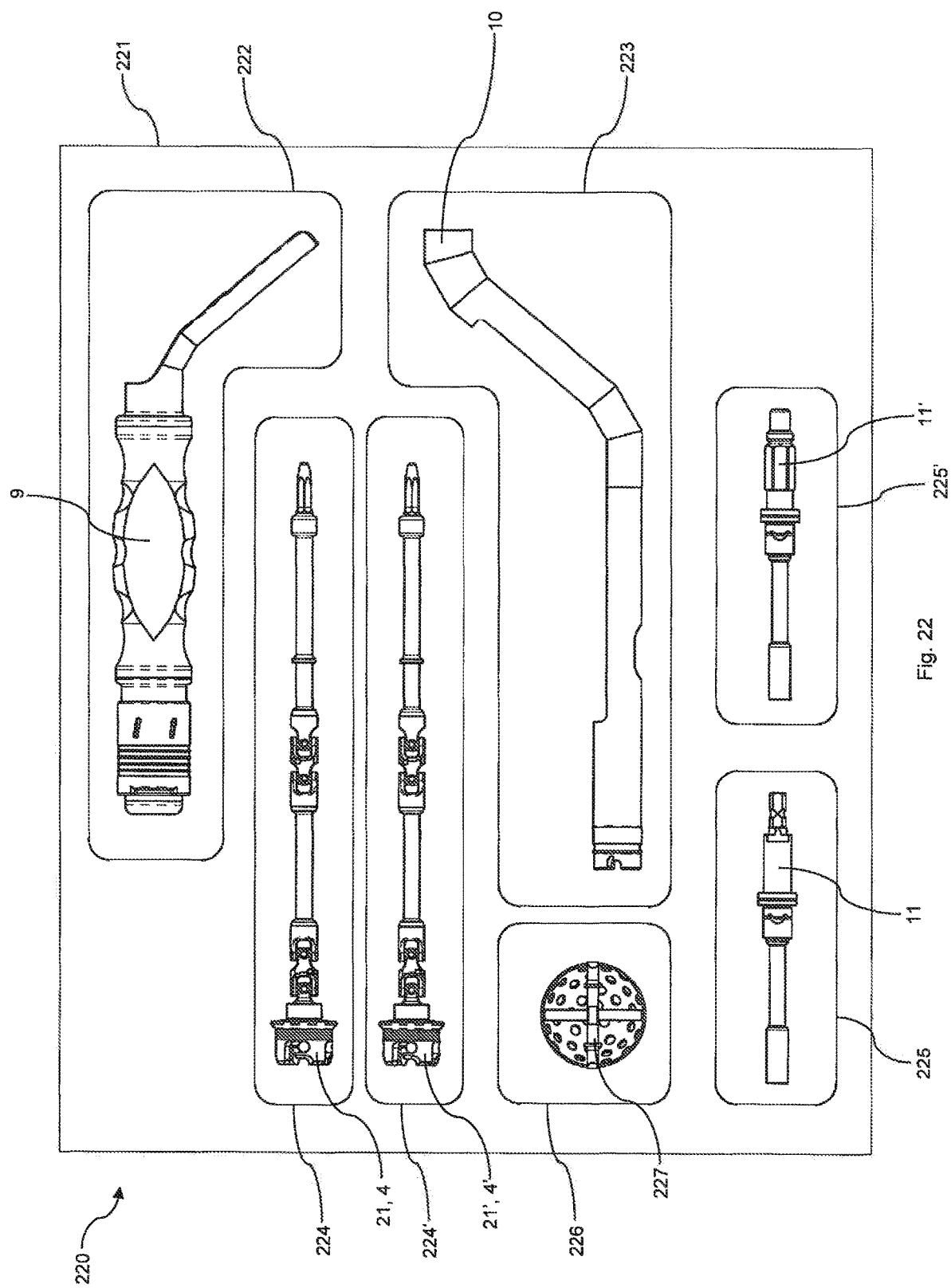
FIG. 22 is a kit of the invention.

Referring now to FIG. 22 (as with FIG. 31 of PCT/IB2016/001143, with reference to the text of the detailed description associated therewith), a kit 220 includes the surgical reamer driver and its components (including some alternate components for alternate configurations), and in addition, a case 221 for organizing and storing the components of the kit. The surgical kit 220 further includes surgical tools 227 (one shown here by duplicates and others having differing outside diameters may be provided) of various sizes and styles, adapted to interface with the surgical tool connector 4. Optionally, an alternative motor coupling 11, 11' are provided, having an alternative connection configuration. Optionally, alternate transmission drive trains 21 and 21' are provided as well, each having an alternate surgical tool connector 4, 4'.

Figure 23:
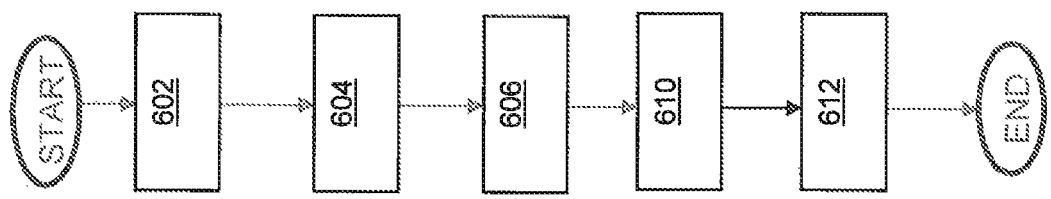
FIG. 23 is a flow chart of the method of the invention.

Referring now to FIG. 23, the method 600 of the invention includes several steps. In a first step 602, the sliding release sleeve 8 is actuated to unlock a handle assembly 9 from a housing 10, thereby permitting the de-encapsulation of a drive train 21 within the housing assembly. In a second step 604, the handle assembly is slid off of the housing thereby effectively de-encapsulating the drive train. In a third step 606, the motor shaft coupling 11 is pulled out of the housing thereby freeing the drive train from axial constraint on one end. In a fourth step 610, the drive train is unsnapped on the one end from a restraint 32 and lifted out of the housing thereby permitting removal of the drive train. In a fifth step 612, the drive train is pulled out of the housing, thus removing the drive train from the housing. Once disassembled, the components may be replaced with alternate components meeting another need or simply cleaned and/or sterilized in preparation for the next use.

The invention may be summarized by the following numbered features:

1. A surgical reamer driver (1) having a distal (3) and proximal end, the driver (1) having:
   a housing assembly (10) in a stand-alone, assembled unit,
   a transmission drive train (21, 21') in a stand-alone, assembled unit enclosed in the housing assembly (10), and having at least one double universal joint (22, 22') and a surgical tool connector (4) at the distal end (3) thereof,
   a motor shaft coupling (11, 11') in a stand-alone, assembled unit at the proximal end thereof, and
   a handle assembly (9) in a stand-alone, assembled unit at the proximal end thereof, these four basic components forming a driver (1) which in a fully assembled state effectively prevents debris from access in the inner workings of the driver (1).

2. The driver (1) of feature 1, wherein the at least one double universal joint (22, 22') of the transmission drive train (21, 21') forms an angle (70, 70') larger than 40° between its input and output shafts (24, 25).

3. The driver (1) of feature 1, wherein a bearing (32), fixed with respect to the housing (3) surrounds a flanged shaft (25), wherein the flange (33) of the shaft (25) acts against the bearing (32) limiting axial movement of the shaft (25).

4. The driver (1) of feature 1, wherein at least a portion of the forks (130, 139) of the double U-joints (22, 22') may be removed and re-affixed with respect to the other portion of the fork, to facilitate assembly.

5. The driver (1) of feature 1, wherein at least one of the forks (130, 139) of the double U-joints (22, 22') comprises friction reducing bearings sleeves (147, 148, 134, 134').6. The driver (1) of feature 5, wherein the double U-joints (22, 22') has bearing sleeves (134, 134') assembled in at least one fork (130, 139) thus reducing friction.

7. The driver (1) of feature 1, wherein the handle assembly (9) includes a bearing (114) which, when assembled over the housing assembly (3, 10) enclosing the drive train (21, 21'), cooperates with bearings (115, 115') in the housing assembly (3, 10) to stabilize the drive train (21, 21').

8. The driver (1) of feature 1, wherein the at least one double universal joint (22, 22') is comprised of two forks which are most widely spaced apart along the transmission axis and oriented 90° with respect to one another.

9. The driver (1) of feature 1, wherein the transmission drive train (21, 21') comprises two double universal joints (22, 22') having its input and output shafts (24, 25) forming an angle (70, 70') larger than 40° and wherein the input shaft (25) of the first double universal joint (22, 22') is offset and parallel to the output shaft (24) of the second double universal joint (22, 22').

10. The driver (1) of feature 1, wherein a drive train assembly (11, 21) comprises an interfacing connection (29)

which when disassembled, divide the drive train assembly (11, 21) into two subcomponents (11, 21), the interfacing connection (29) being disposed between the motor shaft coupling (11) and the surgical tool connector (4) and encapsulated within the housing assembly (10).

11. The driver (1) of feature 1, wherein the handle assembly (9) is disposed over the housing assembly (10) such that axial forces applied by the user to the motor shaft coupling (11, 11') are decoupled from the transmission drive train (21, 21') and applied to the surgical tool connector (4) and wherein the forces applied by a user to the handle (5) are decoupled from both the transmission drive train (21, 21') and the motor shaft coupling (11, 11') and applied to the surgical tool connector (4), preferably through a thrust bearing.

12. The driver (1) of feature 1, wherein the motor shaft coupling (11, 11') rotatably connects the interfacing connection (6, 11, 120) to a drive motor at a proximal end of thereof.

13. The surgical reamer driver (1) of feature 1, wherein axial forces are transmitted through the housing assembly (10) thereby bypassing the transmission drive train (21, 21') and applied, preferably through a bearing, to the surgical tool connector (4).

14. The surgical reamer driver (1) of feature 1, wherein the handle assembly (9) includes a sleeve (8) and a tongue extending distally therefrom which encapsulates the transmission drive train (21, 21') and its interfacing connection (6, 11, 120) within the housing assembly (10).

15. The surgical reamer driver (1) of feature 14, wherein the handle assembly (9) has a sleeve (8) having a tongue extending distally therefrom, the sleeve (8) further encapsulating an elongated opening (160, 161) on one side of the housing assembly (10), the opening permitting removal of the transmission drive train (21, 21') for cleaning, and an opening on an opposite side of the housing assembly (10), the opening allowing finger (51) access to facilitate removable of the drive train (21, 21').

16. The surgical reamer driver (1) of feature 1, wherein the handle assembly (9) transmits axial thrust into the housing assembly (10) and not into the transmission drive train (21, 21') or the motor shaft coupling (11, 11').

17. The surgical tool driver (1) of feature 1, further comprising a release sleeve (8) disposed over a shaft (24, 25) for disconnecting the surgical tool (227) from the surgical tool connector (4), the surgical tool connector (4) further including a locking member having a locking head (190) adapted for coupling with at least one surgical tool (227), such locking member being slidingly disposed and at least significantly enclosed within the center of the driver (1) and closely interfacing therewith so as to minimize seams, gaps or openings, and having an axial range of motion which assures that between an unlock and lock position, the locking head (190) is embedded in the driver (1) in the unlock position and then extends axially outwardly, in snug juxtaposition with the driver (1), to a lock position which is capable of locking a surgical tool (227) to the tool driver (1) in a manner so as to avoid the exposure of a significant seam, gap or opening during activation and so helping prevent debris and/or bone chips from entering the driver (1).

18. The surgical reamer driver (1) of feature 1 further including a sliding release sleeve (8) which locks and unlocks the housing assembly (10) for assembly or disassembly, respectively.

19. The surgical reamer driver (1) of feature 18, wherein the housing assembly (1) has a slotted end in which slots an annular locking feature, such as pins (63, 118, 119, 136, 136') of the handle assembly (9), engages and which locks the handle (5) in a selected angular position wherein further a retainer retains the handle (5) so as to prevent it from freely removing during disassembly.

20. The surgical reamer driver (1) of feature 19, wherein the retainer comprises at least one slot formed so that the slot is smaller than an interfacing diameter of the angular locking feature, preferably a pin (63, 118, 119, 136, 136'), and wherein, a side wall (144, 144') of such slot may be elastically biased to expand an opening of the slot to capture the angular locking feature.

21. A surgical kit (220) comprising the surgical reamer driver (1) of feature 1 together with other components, the kit (220) further comprising a case (221) for organizing and storing the components of the kit (220).

22. The surgical kit (220) of feature 21, further including:
a. surgical tools (227) of various sizes and styles, adapted to interface with the surgical tool connector (4);
b. optionally, an alternative motor coupling (11, 11') having an alternative connection configuration; and
c. optionally, an alternate transmission drive chain (21, 21') having an alternate surgical tool connector (4).

23. A method (600) for disassembling a reamer driver (1) including the steps of:
a. (602) actuating a sliding release sleeve to unlock a handle assembly from a housing assembly, thereby permitting the de-encapsulation of a drive train within the housing assembly;
b. (604) sliding the handle assembly off of the housing thereby effectively de-encapsulating the drive train;
c. (606) pulling a motor shaft coupling out of the housing thereby freeing the drive train from axial constraint on one end;
d. (610) unsnapping the drive train on the one end and lifting the one end out of the housing assembly thereby permitting removal of the drive train; and
e. (612) pulling the drive train out of the housing assembly, thus removing the drive train from the housing assembly.

24. The method (600) of feature 23, wherein the components are cleaned and sterilized. An advantage of the present invention is to provide a reamer driver having fully closed tube in order to avoid penetration of debris and abrasion of soft tissues during use. The reamer driver shown in this application has only 4 components that can be easily replaced when worn out.

Another advantage of the invention is to provide a transmission drive chain having at least a double universal joint linkage that can transmit rotational movement at an angle larger than 40°. The two forks of the universal joint linkage are oriented at 90° from each other.

Another advantage is that the transmission of the load applied on the motor shaft coupling is transmitted to the body of the reamer handle only. The load applied on the handle is also transmitted to the body of the reamer handle only. There is no contact between the motor shaft coupling and the handle assembly. These two cumulated loads are directly transmitted to the reamer head without compressing the universal transmission drive chain, which only transmit the torque applied on the motor shaft coupling.

An advantage of the present invention is to provide a simple reamer driver connection that allows for the quick connect of different type of acetabular reamers from the center of the driver. In comparison to the existing reamer driver connections described in the prior art, the locking mechanism located in the center of the driver prevent debris and bone chips to enter into the mechanism and potentially disconnect the reamer from the reamer driver. It also reduces soft tissue irritation while rotating by limiting the sharp edges of components located around the head of the reamer driver.

In another advantage, the invention provides a locking mechanism in the head of a driver which, unlike the standard lock/release function, can be locked in its open position. This allows the surgeon to insert the cutting tool through a minimal invasive opening first. Then, once locked, the reamer handle can be inserted through the same minimal invasive opening and connected to the cutting tool without activating the locking of the mechanism.

Another advantage of the invention is to provide an easy to assemble and disassemble reamer driver connection for better cleaning and sterilization. The number of components and the risk that parts could be lost have been minimized.

It will be understood that the particular method and devices embodying the invention are shown by way of illustration and not as a limitation of the invention. Although certain illustrative embodiments of the invention have been shown and described here, a wide range of modification, changes and substitutions is contemplated in the foregoing disclosure.

Further, the invention should be considered as comprising all possible combinations of every feature described in the instant specification, appended claims, and/or drawing figures which may be considered new, inventive and industrially applicable.

It should be appreciated that the particular implementations shown and herein described are representative of the invention and its best mode and are not intended to limit the scope of the present invention in any way.

As will be appreciated by skilled artisans, the present invention may be embodied as a system, a device, or a method.

The present invention is described herein with reference to block diagrams, devices, components, and modules, according to various aspects of the invention. It will be understood that each functional block of the blocks diagrams, and combinations of functional blocks in the block diagrams, can be implemented by computer program instructions which may be loaded onto a general purpose computer, special purpose computer, or other programmable data processing apparatus to produce a machine, such that the instructions which execute on the computer or other programmable data processing apparatus create enable the functionality specified in the block diagrams.

Moreover, the system contemplates the use, sale and/or distribution of any goods, services or information having similar functionality described herein.

The specification and figures should be considered in an illustrative manner, rather than a restrictive one and all modifications described herein are intended to be included within the scope of the invention claimed. Accordingly, the scope of the invention should be determined by the appended claims (as they currently exist or as later amended or added, and their legal equivalents) rather than by merely the examples described above. Steps recited in any method or process claims, unless otherwise expressly stated, may be executed in any order and are not limited to the specific order presented in any claim. Further, the elements and/or components recited in apparatus claims may be assembled or otherwise functionally configured in a variety of permutations to produce substantially the same result as the present invention. Consequently, the invention should not be interpreted as being limited to the specific configuration recited in the claims.

Benefits, other advantages and solutions mentioned herein are not to be construed as critical, required or essential features or components of any or all the claims.

As used herein, the terms "comprises", "comprising", or variations thereof, are intended to refer to a non-exclusive listing of elements, such that any apparatus, process, method, article, or composition of the invention that comprises a list of elements, that does not include only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Copyright may be owned by the Applicant(s) or their assignee and, with respect to express Licensees to third parties of the rights defined in one or more claims herein, no implied license is granted herein to use the invention as defined in the remaining claims. Further, vis-à-vis the public or third parties, no express or implied license is granted to prepare derivative works based on this patent specification, inclusive of the appendix hereto and any computer program comprised therein.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A surgical reamer driver having a distal and proximal end, the driver having:
　a housing assembly in a stand-alone, assembled unit, having at least a proximal opening, a distal opening, a lateral opening, and at least one bend,
　a transmission drive train in a stand-alone, assembled unit enclosed in the housing assembly, passing through the distal opening, and having at the at least one bend of the housing, at least one double universal joint comprising two adjacent universal joints connected with a center yoke and a surgical tool connector at the distal end thereof, a motor shaft coupling in a stand-alone, assembled unit, passing through the proximal opening thereof and being rotationally connected and axially, slidably disengageable from the transmission drive train, and a handle assembly in a stand-alone assembled unit, these four basic components forming a driver which in a fully assembled state effectively prevents debris from access in the inner workings of the driver.

2. The driver of claim 1, wherein the at least one double universal joint of the transmission drive train forms an angle larger than 40° between its input and output shafts.

3. The driver of claim 1, wherein a bearing, fixed with respect to the housing surrounds a flanged shaft, wherein the flange of the shaft acts against the bearing limiting axial movement of the shaft.

4. The driver of claim 1, wherein at least a portion of the forks of the double universal joints may be removed and re-affixed with respect to the other portion of the fork, to facilitate assembly.

5. The driver of claim 1, wherein at least one of the forks of the double universal joints comprises friction reducing bearings sleeves.

6. The driver of claim 5, wherein the double universal joints have bearing sleeves assembled in at least one fork thus reducing friction.

7. The driver of claim 1, wherein the handle assembly includes a bearing which, when assembled over the housing assembly enclosing the transmission drive train, cooperates with bearings in the transmission housing assembly to stabilize the drive train.

8. The driver of claim 1, wherein the at least one double universal joint is comprised of two forks which are most widely spaced apart along the transmission axis and oriented 90° with respect to one another.

9. The driver of claim 1, wherein the transmission drive train comprises two double universal joints having its input and output shafts forming an angle larger than 40° and wherein the input shaft of the first double universal joint is offset and parallel to the output shaft of the second double universal joint.

10. The driver of claim 1, wherein the transmission drive train and the motor shaft coupling make up a drive train assembly when engaged together and wherein an interfacing connection permits disengagement of the drive train assembly into two independent subcomponents when disassembled, the interfacing connection being disposed between the motor shaft coupling and the surgical tool connector and encapsulated within the housing assembly.

11. The driver of claim 1, wherein the handle assembly is disposed over the housing assembly such that applied axial forces to the motor shaft coupling are decoupled from the transmission drive train and applied to the surgical tool connector through the housing assembly only and wherein the forces applied by a user to the handle are decoupled from both the transmission drive train and the motor shaft coupling and applied to the surgical tool connector, preferably through a thrust bearing.

12. The driver of claim 1, wherein the motor shaft coupling rotatably connects which is adapted to connect the interfacing connection to a drive motor at a proximal end of thereof.

13. The driver of claim 1, wherein axial forces are transmitted through the housing assembly thereby bypassing the transmission drive train and applied, preferably through a bearing, to the surgical tool connector.

14. The driver of claim 1, wherein the handle assembly includes a sleeve and a tongue extending distally therefrom which encapsulates the transmission drive train and its interfacing connection within the housing assembly.

15. The driver of claim 14, wherein the sleeve and the tongue further closing an elongated opening on one side of the housing assembly, the opening permitting removal of the transmission drive train for cleaning, and an opening on an opposite side of the housing assembly, the opening allowing finger access to facilitate removal of the drive train.

16. The driver of claim 1, wherein the handle assembly transmits axial thrust into the housing assembly and not into the transmission drive train or the motor shaft coupling.

17. The surgical tool connector of claim 1, further comprising a release sleeve disposed over a shaft for disconnecting the surgical tool from the surgical tool connector, the surgical tool connector further including a locking member having a locking head adapted for coupling with at least one surgical tool, such locking member being slidingly disposed and at least significantly enclosed within the center of the driver and closely interfacing therewith so as to minimize seams, gaps or openings, and having an axial range of motion which assures that between an unlock and lock position, the locking head is embedded in the driver in the unlock position and then extends axially outwardly, in snug juxtaposition with the driver, to a lock position which is capable of locking a surgical tool to the tool driver in a manner so as to avoid the exposure of a significant seam, gap or opening during activation and so helping prevent debris and/or bone chips from entering the driver.

18. The driver of claim 1 further including a sliding release sleeve mounted on the handle assembly, the sliding release sleeve comprising a lock/unlock mechanism allowing the handle assembly to be assembled or disassembled from the housing assembly, respectively.

19. The driver of claim 18, wherein the housing assembly has a slotted end in which slots an annular locking feature, such as pins of the handle assembly, engages and which locks a handle of the handle assembly in a selected angular position wherein further a retainer retains the housing assembly with handle assembly so as to prevent it from freely removing during disassembly.

20. The driver of claim 19, wherein the retainer comprises at least one slot formed so that the slot is smaller than an interfacing diameter of the angular locking feature, preferably a pin, and wherein, a side wall of such slot may be elastically biased to expand an opening of the slot to capture the angular locking feature.

21. A surgical kit comprising the surgical reamer driver of claim 1 together with other components, the kit further comprising a case for organizing and storing the components of the kit.

22. The surgical kit of claim 21, further including:
   a. surgical tools of various sizes and styles, adapted to interface with the surgical tool connector;
   b. optionally, an alternative motor coupling having an alternative connection configuration; and
   b. optionally, an alternative motor coupling having an alternative connection configuration; and
   c. optionally, an alternate transmission drive chain having an alternate surgical tool connector.

23. A method for disassembling the reamer driver of claim 1 including the steps of:

a. actuating a sliding release sleeve to unlock a handle assembly from a housing assembly, thereby permitting the de-encapsulation of a drive train within the housing assembly;
b. sliding the handle assembly off of the housing thereby effectively de-encapsulating the drive train;
c. pulling a motor shaft coupling out of the housing thereby freeing the drive train from axial constraint on one end;
d. unsnapping the drive train on the one end and lifting the one end out of the housing assembly thereby permitting removal of the drive train; and
e. pulling the drive train out of the housing assembly, thus removing the drive train from the housing assembly.

24. The method of claim 23, wherein the components are cleaned and sterilized.

25. A surgical reamer driver having a distal and proximal end, the driver having:
a housing assembly in a stand-alone, assembled unit,
a transmission drive train in a stand-alone, assembled unit enclosed in the housing assembly, and having at a bend of the housing, at least one double universal joint comprising two adjacent universal joints connected with a center yoke and a surgical tool connector at the distal end thereof,
a motor shaft coupling in a stand-alone, assembled unit at the proximal end thereof, and
a handle assembly in a stand-alone, assembled unit at the proximal end thereof,
wherein the handle assembly includes a bearing which, when assembled over the housing assembly enclosing the drive train, cooperates with bearings in the housing assembly to stabilize the drive train.

26. A surgical reamer driver having a distal and proximal end, the driver having:
a housing assembly in a stand-alone, assembled unit,
a transmission drive train in a stand-alone, assembled unit enclosed in the housing assembly, and having at a bend of the housing, at least one double universal joint comprising two adjacent universal joints connected with a center yoke and a surgical tool connector at the distal end thereof,
a motor shaft coupling in a stand-alone, assembled unit at the proximal end thereof, and
a handle assembly in a stand-alone, assembled unit at the proximal end thereof, these four basic components forming a driver which in a fully assembled state effectively prevents debris from access in the inner workings of the driver,
wherein further the handle assembly includes a sleeve having a tongue extending distally therefrom which encapsulates the transmission drive train and its interfacing connection within the housing assembly, and
wherein the sleeve encapsulates an elongated opening on one side of the housing assembly, the opening permitting removal of the transmission drive train for cleaning, and an opening on an opposite side of the housing assembly, the opening allowing finger access to facilitate removable of the drive train.

27. A surgical reamer driver having a distal and proximal end, the driver having:
a housing assembly in a stand-alone, assembled unit,
a transmission drive train in a stand-alone, assembled unit enclosed in the housing assembly, and having at a bend of the housing, at least one double universal joint comprising two adjacent universal joints connected with a center yoke and a surgical tool connector at the distal end thereof, comprising two adjacent universal joints connected with a center yoke and a surgical tool connector at the distal end thereof,
a motor shaft coupling in a stand-alone, assembled unit at the proximal end thereof, and
a handle assembly in a stand-alone, assembled unit at the proximal end thereof, these four basic components forming a driver which in a fully assembled state effectively prevents debris from access in the inner workings of the driver,
the reamer driver further including a sliding release sleeve which locks and unlocks the housing assembly for assembly or disassembly, respectively,
wherein the housing assembly has a slotted end in which slots an annular locking feature, such as pins of the handle assembly, engages and which locks the handle in a selected angular position wherein further a retainer retains the handle so as to prevent it from freely removing during disassembly,
wherein the retainer comprises at least one slot formed so that the slot is smaller than an interfacing diameter of the angular locking feature, preferably a pin, and wherein, a side wall of such slot may be elastically biased to expand an opening of the slot to capture the angular locking feature.

28. A surgical reamer driver having a distal and proximal end, the driver having:
a housing assembly in a stand-alone, assembled unit,
a transmission drive train in a stand-alone, assembled unit enclosed in the housing assembly, and having at a bend of the housing, at least one double universal joint comprising two adjacent universal joints connected with a center yoke and a surgical tool connector at the distal end thereof,
a motor shaft coupling in a stand-alone, assembled unit at the proximal end thereof,
a handle assembly in a stand-alone, assembled unit at the proximal end thereof, these four basic components forming a driver which in a fully assembled state effectively prevents debris from access in the inner workings of the driver,
the reamer driver further including a sliding release sleeve which locks and unlocks the housing assembly for assembly or disassembly, respectively, and
wherein the housing assembly has a slotted end in which slots an annular locking feature, such as pins of the handle assembly, engages and which locks the handle in a selected angular position wherein further a retainer retains the handle so as to prevent it from freely removing during disassembly.

* * * * *